United States Patent
Okuda et al.

(10) Patent No.: US 12,002,199 B2
(45) Date of Patent: Jun. 4, 2024

(54) METHODS, APPARATUSES, AND SYSTEMS FOR 3-D PHENOTYPING AND PHYSIOLOGICAL CHARACTERIZATION OF BRAIN LESIONS AND SURROUNDING TISSUE

(71) Applicant: The Board of Regents of the University of Texas System, Austin, TX (US)

(72) Inventors: Darin T. Okuda, Coppell, TX (US); Dinesh K. Sivakolundu, East Haven, CT (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 517 days.

(21) Appl. No.: 17/281,022

(22) PCT Filed: Sep. 30, 2019

(86) PCT No.: PCT/US2019/053826
§ 371 (c)(1),
(2) Date: Mar. 29, 2021

(87) PCT Pub. No.: WO2020/069509
PCT Pub. Date: Apr. 2, 2020

(65) Prior Publication Data
US 2021/0343008 A1 Nov. 4, 2021

Related U.S. Application Data

(60) Provisional application No. 62/738,270, filed on Sep. 28, 2018.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4836* (2013.01); *G06T 7/11* (2017.01);
(Continued)

(58) Field of Classification Search
CPC ......... G06T 7/0012; G06T 7/11; G06T 7/149; G06T 2207/10088; G06T 2207/20084;
(Continued)

(56) References Cited

U.S. PATENT DOCUMENTS

2004/0254446 A1 12/2004 Miller et al.
2006/0088083 A1 4/2006 Ikezaki
(Continued)

FOREIGN PATENT DOCUMENTS

WO 2018005939 A1 1/2018

OTHER PUBLICATIONS

International Patent Application No. PCT/US2019/053826 "International Search Report and Written Opinion" dated Dec. 13, 2019, 8 pages.

*Primary Examiner* — Ming Y Hon
(74) *Attorney, Agent, or Firm* — POLSINELLI PC

(57) ABSTRACT

The present disclosure includes methods, apparatuses, and systems for three-dimensional phenotyping and physiologic characterization of brain lesions and tissue encompassing one or more enlarged boundaries surrounding the brain lesion to study the metabolic and physiologic profiles from tissue within and around lesions and their impacts on lesion shape and surface texture. The non-invasive biomarker blood-oxygen their impacts on lesion shape and surface texture. The non-invasive biomarker blood-oxygen-level-dependent (BOLD) slope was used to metabolically characterize lesions. Metabolically active lesions with more intact tissue and myelin architecture have more symmetrical shapes and more complex surface textures compared to
(Continued)

metabolically inactive lesions with less intact tissue and myelin architecture. The association of lesions' shapes and surface features with their metabolic signatures aid in the translation of MRI data to clinical management by providing information related to metabolic activity, lesion age, and risk for disease reactivation and self-repair.

28 Claims, 22 Drawing Sheets

(51) Int. Cl.
    *G06T 7/11*      (2017.01)
    *G06T 7/149*      (2017.01)

(52) U.S. Cl.
    CPC .... *G06T 7/149* (2017.01); *G06T 2207/10088* (2013.01); *G06T 2207/20084* (2013.01); *G06T 2207/30016* (2013.01); *G06T 2207/30096* (2013.01); *G06T 2207/30104* (2013.01)

(58) Field of Classification Search
    CPC . G06T 2207/30016; G06T 2207/30096; G06T 2207/30104; A61B 5/4836
    See application file for complete search history.

(56) References Cited

U.S. PATENT DOCUMENTS

| | | |
|---|---|---|
| 2009/0246138 A1 | 10/2009 | Santosh et al. |
| 2014/0235529 A1* | 8/2014 | Wilson .................. A61P 13/12 |
| | | 514/1.9 |
| 2016/0220115 A1* | 8/2016 | Fisher .................. A61B 5/0263 |
| 2023/0259864 A1* | 8/2023 | Decrop ................ A61B 5/0022 |
| | | 705/7.41 |

\* cited by examiner

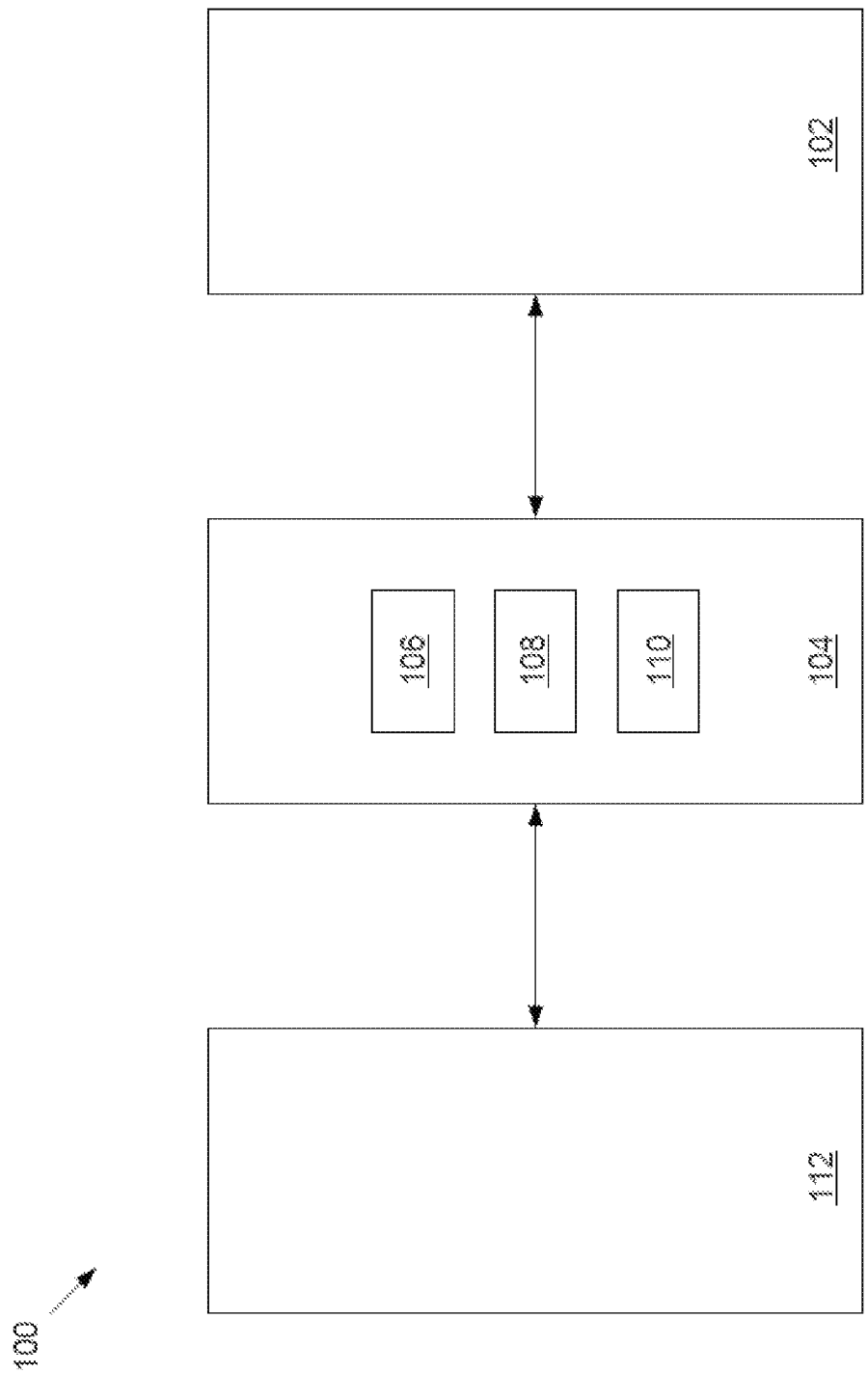

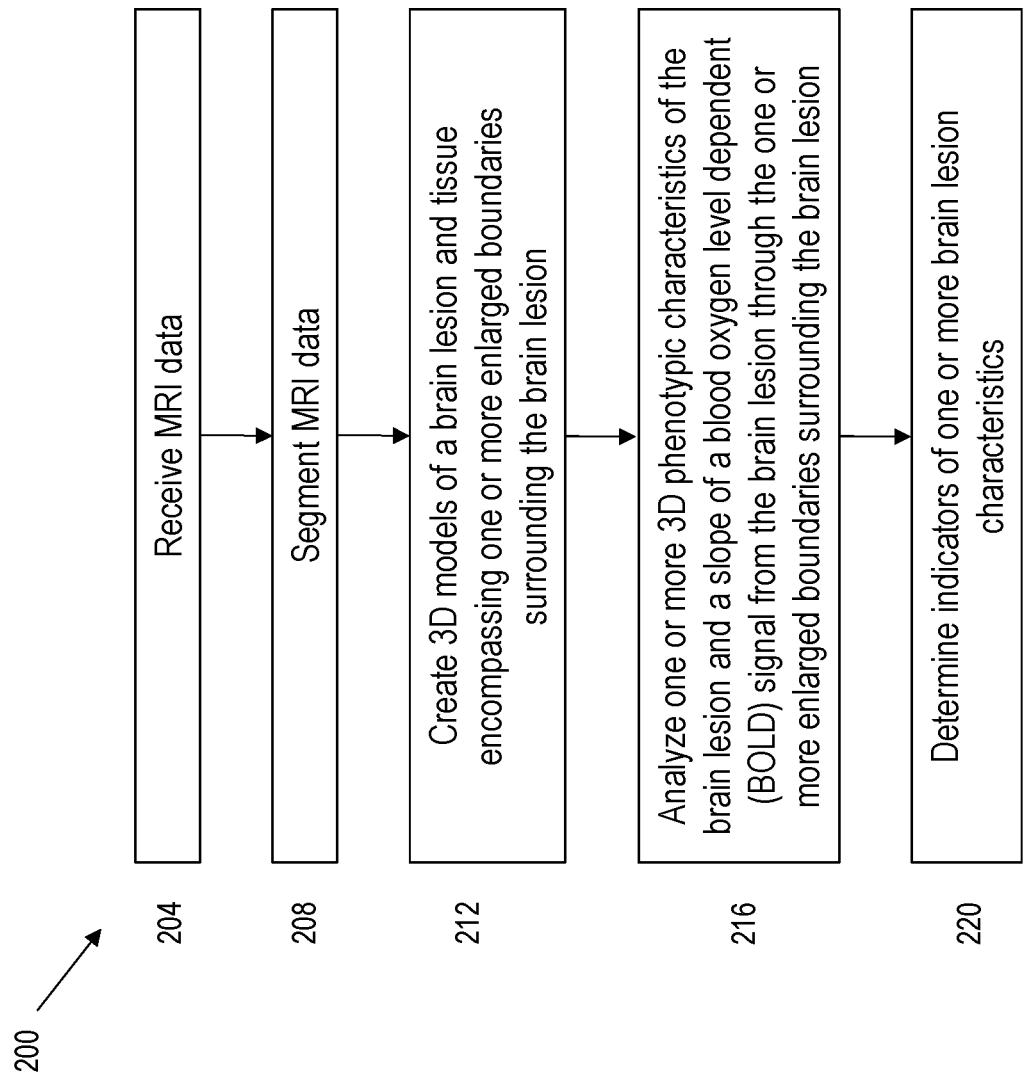

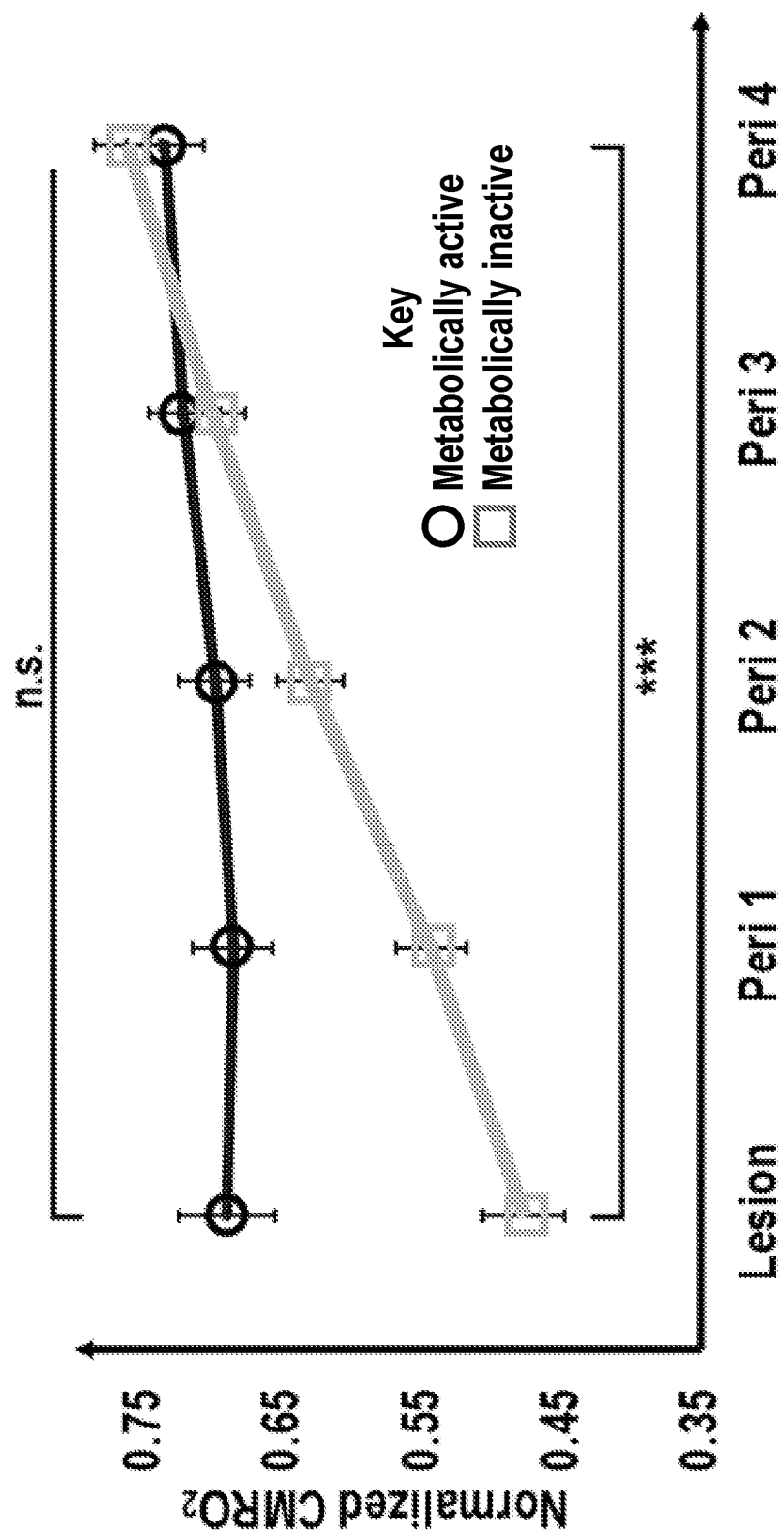

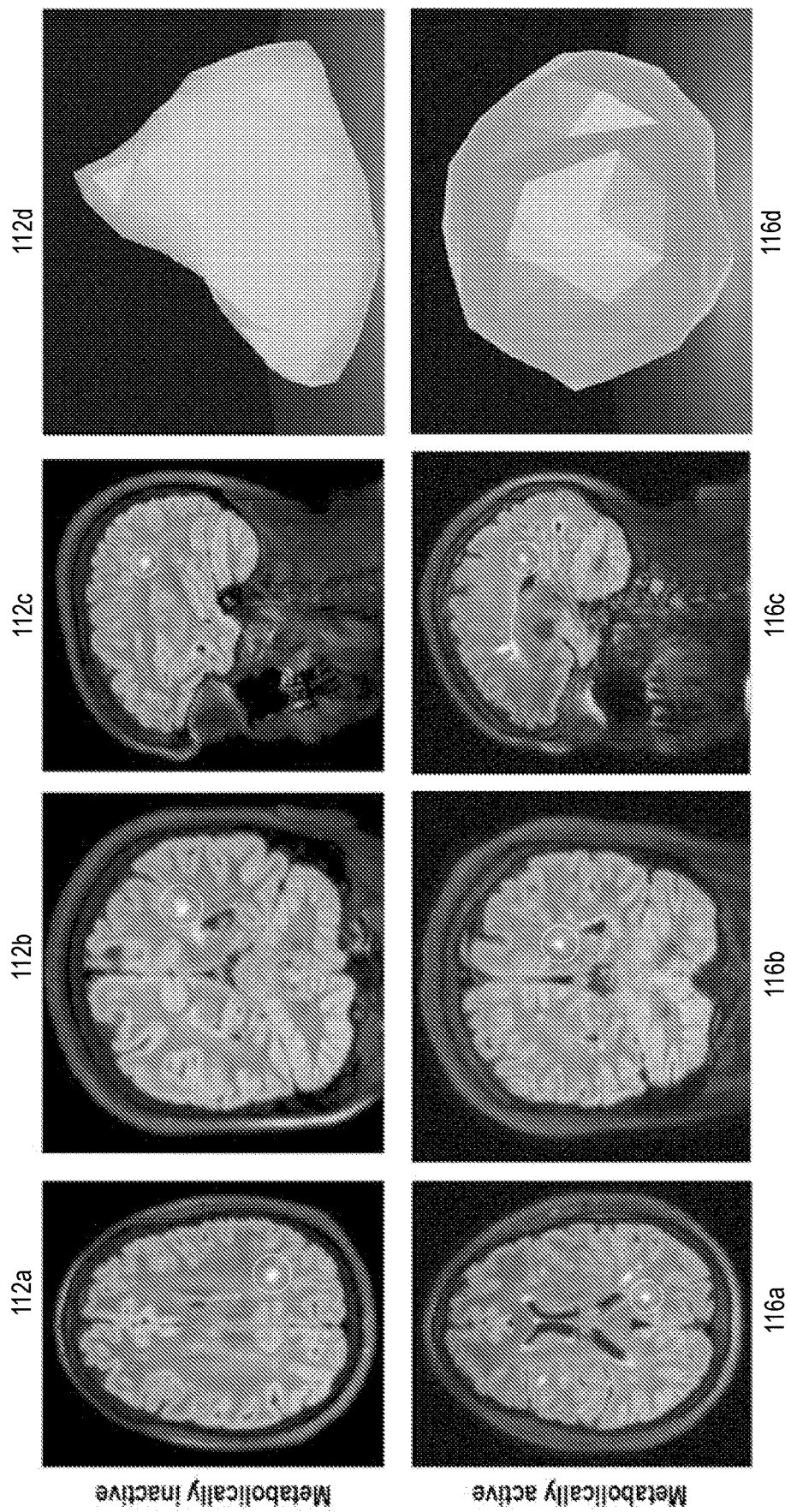

METHODS, APPARATUSES, AND SYSTEMS FOR 3-D PHENOTYPING AND PHYSIOLOGICAL CHARACTERIZATION OF BRAIN LESIONS AND SURROUNDING TISSUE

The present application is a national phase application under 35 U.S.C. § 371 of International Application No. PCT/US2019/053826, filed Sep. 30, 2019, which claims the benefit of priority to U.S. Provisional Application No. 62/738,280, filed Sep. 28, 2018, both of which are hereby incorporated by reference in their entireties.

TECHNICAL FIELD

The present application relates generally to methods, apparatuses, and systems for characterizing a brain lesion, and more particularly, but not by way of limitation, to three-dimensionally (3D) phenotyping and physiologically characterizing brain lesions and the surrounding tissue.

BACKGROUND

Multiple sclerosis (MS) is an autoimmune inflammatory disorder of the central nervous system that results in injury to myelin, nerve fibers, and glial cells, affecting nearly 1 million individuals in the United States. Symptoms frequently include focal neurologic deficits, including visual, motor and sensory disturbances. Autonomic dysregulation and cognitive impairment might also occur. Clinicians depend on magnetic resonance imaging (MRI) for MS diagnosis, disease surveillance in the presence or absence of treatment, and prediction of future clinical outcomes. Disease progression, punctuated by the development of contrast-enhancing or new $T_2$-lesions commonly results in a change in disease-modifying treatment. Currently, conventional MRI techniques employed in MS are limited by false positives due to high sensitivity to white-matter hyperintensities and reduced specificity regarding disease origin. Such techniques are also limited by the forced perspectives in two-dimensional (2D) planes (axial, sagittal and coronal). In addition, the magnitude of axonal and glial injury resulting from in-situ demyelination in existing or newly developed $T_2$-hyper-intensities is unclear.

Recently, three-dimensional (3D) phenotyping of MS lesions has provided a more comprehensive view of their shape and surface features than has previously been possible. This additional perspective has led to the observation that some MS lesions assume an amorphous structure with complex surface features. Such observations suggest that important information regarding MS diagnosis and disease progression might be possible based on lesion features including their shape, symmetry, and surface texture. Understanding the degree of microstructural injury, physiologic dysfunction, and myelin repair is essential for ascertaining the clinical significance of these features.

A variety of techniques have indicated changes to the structural and functional characteristics of tissue both inside and outside of lesions. For instance, there is evidence that myelin injury extends beyond the lesion boundaries at varying distances from MS lesion centers. Magnetization transfer imaging measures a ratio of the macromolecule-bound protons (i.e., myelin) to free water protons in tissue. Thus, a higher magnetization transfer ratio (MTR) suggests more myelin. Using this technique, Bagley and colleagues showed increasing MTR at increasing distances from MS lesion centers. This result suggests that myelin injury extends beyond the lesion boundary and this injury gradually reduces moving outwards from the lesion center. In addition, studies using diffusion tensor imaging showed altered white-matter integrity in tissue outside MS lesions. Such results suggest that MS-related myelin and axonal injury exist beyond lesion boundaries. Histopathological studies have also identified different immunological injury patterns within lesions. Thus, there is substantial evidence that heterogeneity in myelination and axonal injury exists inside and outside MS lesions. Currently, no imaging markers are capable of characterizing this heterogeneity.

Calibrated dual-echo functional MRI (cfMRI) provides a means by which to characterize lesion heterogeneity because it allows near-simultaneous measures of blood-oxygen-level-dependent signal (BOLD) and cerebral blood flow (CBF), permitting calculation of the cerebral metabolic rate of oxygen (CMRO2) using the deoxyhemoglobin dilution model. Because cfMRI provides metabolic measures and has high spatial resolution, it allows metabolic characterization of lesions. In cfMRI, the T2*-weighted BOLD signal results from local magnetic field susceptibility effects of paramagnetic deoxyhemoglobin and diamagnetic oxyhemoglobin in the veins, physiologically providing a measure of venous blood oxygen content voxelwise. The acquired BOLD signal depends on upstream factors including 1) arterial CBF, 2) cellular oxygen extraction from the capillaries and, 3) CMRO2, thus making BOLD signal a biomarker of physiologic integrity.

SUMMARY

This disclosure includes implementations of methods and configurations of apparatuses and systems for three-dimensionally phenotyping and physiologically characterizing brain lesions and tissue encompassing surrounding boundaries. Non-limiting examples of conditions that benefit from this disclosure include, but are not limited to, multiple sclerosis, aging, small vessel disease, migraine headaches, and other non-specific white matter lesion etiologies.

The clinical management of multiple sclerosis (MS) currently involves disease characterization based on two-dimensional forced-perspectives of magnetic resonance imaging (MRI) data. Such views fail to provide an understanding of the complexity of lesion shape and surface texture, the magnitude of injury within and around lesions, the extent of alterations in the underlying metabolism, and the potential for self-remyelination and recovery. In the present disclosure, a novel three-dimensional (3D) lesion phenotyping approach was utilized and coupled with physiologic measures to study the metabolic and physiologic profiles from tissue within and around lesions and their impacts on lesion shape and surface texture. A non-invasive biomarker called blood-oxygen-level-dependent (BOLD) slope was identified to metabolically characterize brain lesions. BOLD slope is defined as the rate of change in venous blood oxygen content from the lesion tissue to its surrounding brain tissue. Metabolically active lesions demonstrating positive BOLD slopes had higher cerebral metabolic rate of oxygen and higher cerebral blood flow compared to inactive lesions demonstrating negative slopes. Results indicated that metabolically active lesions with more intact tissue and myelin architecture have more symmetrical shapes and more complex surface textures compared to metabolically inactive lesions with less intact tissue and myelin architecture. The association of lesions' shapes and surface features with their metabolic signatures suggest the prospect for immediate translation of MRI data to clinical management by providing information related to metabolic activity, lesion age, and risk for disease reactivation and self-repair. The present disclosure further provides a platform for disease surveillance and outcome quantification involving therapeutics aimed at myelin repair. The metabolic information acquired from the periphery of MRI lesions may inform on disease advancement or stability, prompting a switch from one disease modifying therapy to another agent. This may involve the use of treatments that are more highly effective, including chemotherapeutic medications or potent immunomodulatory regimens aimed at suppressing disease activity or treatments associated with better safety profiles. The method may also allow for the determination of treatment effects from prescribed therapies or investigational medications aimed at myelin, axonal, or tissue repair. An alternate approach to the use of these data may involve the cessation of treatment in certain age groups if the acquired findings suggest disease stability. Additionally, the metabolic profiles from these lesions and their surrounding tissue may inform on the risk for more advanced brain aging, specifically regional brain volume reductions involving surrounding tissue or total brain volumes.

Some embodiments include a system for determining characteristics of a brain lesion and tissue encompassing boundaries surrounding the brain lesion in three dimensions, the system having a computer system comprising at least one processor configured to receive data from a magnetic resonance imaging (MRI) machine configured to generate one or more series of images corresponding to a structural and a functional characteristic of a brain lesion and tissue encompassing one or more enlarged boundaries surrounding the brain lesion, the brain lesion having an outer boundary and at least part of each of the one or more boundaries surrounding the brain lesion being offset by a given distance from the outer boundary of the brain lesion; segment the received data to isolate the portion of the received data corresponding to the brain lesion and the tissue surrounding the brain lesion within the one or more enlarged boundaries; create, based on the segmented data, one or more three-dimensional (3D) models of the brain lesion and the tissue surrounding the brain lesion within the one or more enlarged boundaries; analyze, based on the one or more 3D models, one or more 3D phenotypic characteristics of the brain lesion and a slope of a blood oxygen level dependent (BOLD) signal from within the brain lesion through the one or more enlarged boundaries; and determine, based on the one or more 3D phenotypic characteristics and the slope, indicators of one or more characteristics selected from the group of characteristics consisting of: lesion age, extent of injury, remyelination capacity, tissue integrity within the brain lesion, tissue integrity within tissue surrounding the brain lesion, and metabolic activity of the brain lesion within tissue surrounding the brain lesion.

In some configurations, a majority of each of the one or more boundaries surrounding the brain lesion can be offset by a given distance from the outer boundary of the brain lesion. In some configurations, all of each of the one or more boundaries surrounding the brain lesion can be offset by a given distance from the outer boundary of the brain lesion.

In some configurations, the one or more series of images are generated from one or more structural imaging sequences and one or more functional imaging sequences. The one or more structural imaging sequences may include fluid attenuated inversion recovery (FLAIR), magnetization-prepared rapid acquisition gradient-echo (MPRAGE), and diffusion kurtosis imaging sequences. Other structural and/or functional imaging sequences may be included to further enhance structural and/or functional details of the one or more series of images. In some configurations, the one or more functional imaging sequences include pseudo-continuous arterial spin labeling (pCASL) or continuous arterial spin labeling (CASL) to generate images corresponding to cerebral blood flow (CBF) and functional imaging sequences to generate blood oxygen level dependent (BOLD) data.

In some configurations, segmentation is performed on three-dimensional (3D) fluid attenuated inversion recovery (FLAIR) images via implementing geodesic active contour methodology.

In some configurations, the received data includes a series of two-dimensional (2D) images, and the one or more three-dimensional (3D) models is derived from the series of 2D images. In some configurations, each of the series of two-dimensional (2D) images is given a thickness and assembled to define the one or more 3D models capable of being exported into stereolithographic format.

In some configurations, the one or more 3D models include segmented data from 3D $T_1$-weighted, $T_2$-weighted, and fluid attenuated inversion recovery (FLAIR) images. In some configurations, the one or more 3D models can further include segmented data from 3D $T_2$-weighted fluid attenuated inversion recovery (3D $T_2$ FLAIR), $T_1$-weighted magnetization-prepared rapid acquisition gradient-echo (MPRAGE), and diffusion kurtosis (DK) images.

In some configurations, one or more processors can be configured to isolate the brain lesion to create the one or more three-dimensional (3D) models of the brain lesion and the tissue encompassing the one or more enlarged boundaries surrounding the brain lesion based on the segmented data generated from 3D $T_2$-weighted fluid attenuated inversion recovery (3D $T_2$ FLAIR).

In some configurations, one or more processors can be configured to create the one or more three-dimensional (3D) models of the brain lesion and the tissue encompassing the one or more enlarged boundaries surrounding the brain lesion based on the segmented data generated from $T_1$-weighted magnetization-prepared rapid acquisition gradient-echo (MPRAGE) imaging.

In some configurations, one or more processors can be configured to determine an indicator of tissue integrity within the brain lesion by measuring white matter microstructure integrity via diffusion kurtosis imaging (DKI).

In some configurations, the slope of the blood oxygen level dependent (BOLD) signal is calculated using the formula $$\text{BOLD slope} = \frac{\sum_{i=region}^{n}(\text{BOLD}_i - \overline{\text{BOLD}})(T_i - \overline{T})}{\sum_{i=region}^{n}(\text{BOLD}_i - \overline{\text{BOLD}})}$$

where regions are the brain lesions and their associated perimeters, n is the number of regions, $\text{BOLD}_i$ is the average BOLD signal in the region and $\overline{\text{BOLD}}$ is the average BOLD signal across all regions, $T_i$ is the thickness of the concentric voxel layer.

In some configurations, a cerebral metabolic rate of oxygen ($CMRO_2$) is calculated using the formula $$\frac{\Delta\text{BOLD}}{\text{BOLD}_0} = M\left(1 - \left[\frac{\Delta CMRO_2}{CMRO_{2|0}}\right]^\beta \left[\frac{\Delta CBF}{CBF_0}\right]^{\alpha-\beta}\right)$$

where α=0.38 is an empirically-derived constant linking CBF and cerebral blood volume; β=1.3 is an empirically-derived constant related to vascular exchange and susceptibility of deoxyhemoglobin at 3T; and M is a subject-specific scaling factor dependent upon the washout of resting deoxyhemoglobin determined by a hypercapnia calibration experiment. The hypercapnia induced changes in the blood oxygen level dependent (BOLD) signal and the cerebral blood flow (CBF) can be used to calculate a subject-specific scaling factor M using the formula $$M = \frac{\frac{\Delta BOLD}{BOLD_0}}{\left(\frac{CBF}{CBF_0}\right)^{\alpha-\beta}}$$

where the subject-specific scaling factor M and the average blood oxygen level dependent (BOLD) and the cerebral blood flow (CBF) data can be used to calculate $CMRO_2$ within and around the brain lesion using the formula $$\frac{CMRO_2}{CMRO_{2|gm}} = \left(1 - \frac{\frac{\Delta BOLD}{BOLD_{gm}}}{M}\right)^{\frac{1}{\beta}} \left(\frac{CBF}{CBF_{gm}}\right)^{1-\frac{\alpha}{\beta}}$$

In some configurations, the one or more 3D phenotypic characteristics include lesion volume, lesion surface texture, and/or lesion shape. Manifold harmonics transform (MHT) descriptors can be used to quantify lesion shape from a 3D lesion geometry via eigenfunctions of Laplace-Beltrami operators. In some configurations, one or more processors can be configured to sort eigenvalues in ascending order and select one or more eigenvectors corresponding to the smallest eigenvalues to reconstruct an original shape of the brain lesion.

Some implementations of the present methods include a method of determining characteristics of brain lesions and tissue encompassing boundaries surrounding the brain lesion in a patient, the method including scanning a portion of the patient with a magnetic resonance imaging (MRI) machine configured to generate data corresponding to a structural and a functional characteristic of a brain lesion of the patient and tissue encompassing one or more enlarged boundaries surrounding the brain lesion, the brain lesion having an outer boundary and at least part of each of the one or more boundaries surrounding the brain lesion being offset by a given distance from the outer boundary of the brain lesion; segmenting the generated data to isolate the portion of the generated data corresponding to the brain lesion and the tissue surrounding the brain lesion within the one or more enlarged boundaries; creating, based on the segmented data, one or more three-dimensional (3D) models of the brain lesion and the tissue surrounding the brain lesion within the one or more enlarged boundaries; analyzing, based on the one or more 3D models, one or more 3D phenotypic characteristics of the brain lesion and a slope of a blood oxygen level dependent (BOLD) signal from within the brain lesion through the one or more enlarged boundaries; and determining, based on the one or more 3D phenotypic characteristics and the slope, indicators of one or more characteristics selected from the group of characteristics consisting of: lesion age, extent of injury, remyelination capacity, tissue integrity within the brain lesion, tissue integrity within tissue surrounding the brain lesion, and metabolic activity of the brain lesion within tissue surrounding the brain lesion.

In some implementations, a majority of each of the one or more boundaries surrounding the brain lesion can be offset by a given distance from the outer boundary of the brain lesion. In some implementations, all of each of the one or more boundaries surrounding the brain lesion can be offset by a given distance from the outer boundary of the brain lesion. In some implementations, the one or more enlarged boundaries surrounding the brain lesion each include a region defined as a 3 mm concentric voxel layer. In some implementations, the one or more enlarged boundaries surrounding the brain lesion include a first boundary, a second boundary, a third boundary, and a fourth boundary.

In some implementations, scanning includes one or more structural imaging sequences and one or more functional imaging sequences. In some implementations, the one or more structural imaging sequences include fluid attenuated inversion recovery (FLAIR), magnetization-prepared rapid acquisition gradient-echo (MPRAGE), and diffusion kurtosis imaging sequences. In some implementations, the one or more functional imaging sequences comprise pseudo-continuous arterial spin labeling (pCASL) or continuous arterial spin labeling (CASL) to generate images corresponding to cerebral blood flow (CBF) and functional imaging sequences to generate blood oxygen level dependent (BOLD) data.

In some implementations, segmentation can be performed on three-dimensional (3D) fluid attenuated inversion recovery (FLAIR) images via implementing geodesic active contour methodology. In some implementations, the generated data includes a series of two-dimensional (2D) images, and the one or more three-dimensional (3D) models is derived from the series of 2D images. In some implementations, each of the series of two-dimensional (2D) image is given a thickness and assembled to define the one or more 3D models capable of being exported into stereolithographic format. In some implementations, the one or more 3D models include segmented data from 3D $T_1$-weighted, $T_2$-weighted, and fluid attenuated inversion recovery (FLAIR) images. In some implementations, the one or more 3D models further include segmented data from 3D $T_2$-weighted fluid attenuated inversion recovery (3D $T_2$ FLAIR), $T_1$-weighted magnetization-prepared rapid acquisition gradient-echo (MPRAGE), and diffusion kurtosis (DK) images.

In some implementations, scanning includes 3D $T_2$-weighted fluid attenuated inversion recovery (3D $T_2$ FLAIR) to isolate the brain lesion to create the one or more three-dimensional (3D) models of the brain lesion and the tissue encompassing the one or more enlarged boundaries surrounding the brain lesion. In some implementations, scanning further includes $T_1$-weighted magnetization-prepared rapid acquisition gradient-echo (MPRAGE) imaging to produce anatomical images of the brain lesion and the tissue encompassing the one or more enlarged boundaries surrounding the brain lesion. In some implementations, scanning further includes diffusion kurtosis imaging (DKI) to measure white matter microstructure integrity within the brain lesion.

In some implementations, analyzing includes calculating a cerebral blood flow (CBF) value and a cerebral metabolic rate of oxygen ($CMRO_2$) value.

In some implementations, the slope of the blood oxygen level dependent (BOLD) signal is calculated using the formula $$\text{BOLD slope} = \frac{\sum_{i=region}^{n}(\text{BOLD}_i - \overline{\text{BOLD}})(T_i - \overline{T})}{\sum_{i=region}^{n}(\text{BOLD}_i - \overline{\text{BOLD}})}$$

where regions are the brain lesions and their associated perimeters, n is the number of regions, $\text{BOLD}_i$ is the average BOLD signal in the region and $\overline{\text{BOLD}}$ is the average BOLD signal across all regions, $T_i$ is the thickness of the concentric voxel layer.

In some implementations, a cerebral metabolic rate of oxygen ($CMRO_2$) is calculated using the formula $$\frac{\Delta\text{BOLD}}{\text{BOLD}_0} = M\left(1 - \left[\frac{\Delta CMRO_2}{CMRO_{2|0}}\right]^\beta \left[\frac{\Delta CBF}{CBF_0}\right]^{\alpha-\beta}\right)$$

where $\alpha=0.38$ is an empirically-derived constant linking CBF and cerebral blood volume; $\beta=1.3$ is an empirically-derived constant related to vascular exchange and susceptibility of deoxyhemoglobin at 3T; and M is a subject-specific scaling factor dependent upon the washout of resting deoxyhemoglobin determined by a hypercapnia calibration experiment. The hypercapnia induced changes in the blood oxygen level dependent (BOLD) signal and the cerebral blood flow (CBF) can be used to calculate a subject-specific scaling factor M using the formula $$M = \frac{\frac{\Delta\text{BOLD}}{\text{BOLD}_0}}{\left(\frac{CBF}{CBF_0}\right)^{\alpha-\beta}}$$

where the subject-specific scaling factor M and the average blood oxygen level dependent (BOLD) and the cerebral blood flow (CBF) data can be used to calculate $CMRO_2$ within and around the brain lesion using the formula $$\frac{CMRO_2}{CMRO_{2|gm}} = \left(1 - \frac{\frac{\Delta\text{BOLD}}{\text{BOLD}_{gm}}}{M}\right)^{\frac{1}{\beta}} \left(\frac{CBF}{CBF_{gm}}\right)^{1-\frac{\alpha}{\beta}}$$

In some implementations, the one or more 3D phenotypic characteristics include lesion volume, lesion surface texture, and/or lesion shape. Manifold harmonics transform (MHT) descriptors can be used to quantify lesion shape from a 3D lesion geometry via eigenfunctions of Laplace-Beltrami operators. In some implementations, eigenvalues are sorted in ascending order and one or more eigenvectors corresponding to the smallest eigenvalues are selected to reconstruct an original shape of the brain lesion.

Some implementations of the present methods include a method of treating brain lesions in a patient, the method including administering a treatment to the patient in response to a determination of one or more physiological characteristics of the brain lesions by any one of the disclosed methods. In some implementations, the treatment is switched, based on the determination step, from a disease modifying therapeutic agent to a different disease modifying therapeutic agent. In some implementations, the treatment includes one or more chemotherapeutic drugs and/or immunomodulatory agents.

In some implementations, the method further includes determining, based on the one or more 3D phenotypic characteristics and the slope, treatment effects from one or more prescribed therapies and/or one or more investigational medications aimed at myelin, axonal, and/or tissue repair.

In some implementations, the method further includes cessation of the treatment in certain age groups if an association of the one or more 3D phenotypic characteristics and the slope suggest disease stability.

In some implementations, lesion age, extent of injury, remyelination capacity, tissue integrity within the brain lesion, tissue integrity within tissue encompassing one or more enlarged boundaries surrounding the brain lesion, and metabolic activity of the brain lesion and tissue encompassing one or more enlarged boundaries surrounding the brain lesion are determined using artificial intelligence, machine learning, and/or deep learning techniques.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any configuration or implementation of the present devices, apparatuses, kits, and methods, the term "substantially" may be substituted with "within [a percentage] of" what is specified, where the percentage includes 0.1, 1, 5, and/or 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus, device, or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, an apparatus, device, or structure that is configured in a certain way is configured in at least that way, but it can also be configured in other ways than those specifically described.

Any configuration or implementation of any of the present devices, apparatuses, kits, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the configurations described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure.

Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the configurations depicted in the figures.

FIG. 1 depicts an exemplary system for determining characteristics of brain lesions according to an embodiment of the disclosure.

FIG. 2 depicts an exemplary method for determining characteristics of brain lesions according to an embodiment of the disclosure.

FIG. 5C shows the relationship of cerebral metabolic rate of oxygen ($CMRO_2$) from the MS brain lesion to its Perimeters (Peri) 1-4 in metabolically active brain lesions and metabolically inactive brain lesions.

FIG. 6A shows examples of metabolically active and inactive MS brain lesions in 2D and 3D views demonstrating the marked underrepresentation of the MS brain lesion shape and texture in 2D forced perspectives of MRI.

DESCRIPTION OF ILLUSTRATIVE EMBODIMENTS

Figure 3B:
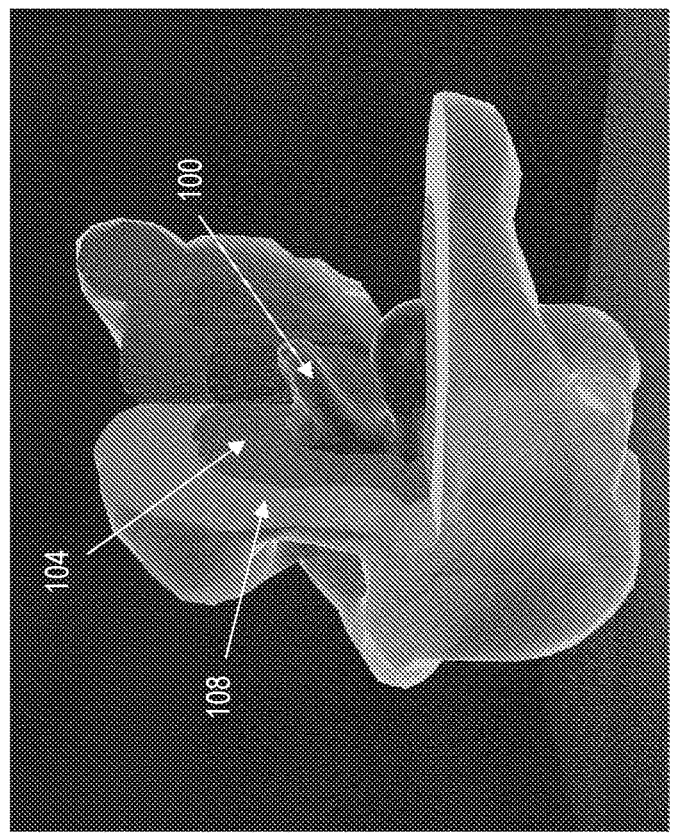
FIG. 3B shows a representation of the MS brain lesion of FIG. 3A and its surrounding boundaries (Perimeters 1-2) as 3 mm concentric layers mirroring the three-dimensional (3D) shape around the MS brain lesion.

Currently, the clinical management of MS patients is limited by 2D forced perspectives of MRI views that markedly underrepresent the complexity of lesion shape and texture. Observations made from the 2D perspective fail to appreciate the magnitude of injury within and around MS lesions, the extent of alterations in the underlying metabolism, the potential for self-remyelination and recovery, and the long-term outcomes related to the impact of lesions on their surrounding brain tissue.

The present disclosure describes a practical and innovative approach to assessing physiologic data from the lesion tissue and one or more enlarged boundaries surrounding the brain lesion. In some implementations, the boundaries can be defined as surrounding concentric perimeters extending from the surface of a 3D MS lesion. The association of lesion shape and surface features with its metabolic signatures may aid in the immediate translation of MRI data to clinical management by providing information related to metabolic activity. The inclusion of an unconventional lesion-isolation technique enabled the direct extraction of lesions in 3D without reconstruction through 2D slices and allowed for lesion traits to be phenotyped.

In some implementations of the present configurations, the novel 3D approach to the characterization of MS lesion phenotypes offers a more accurate reflection of the underlying microstructural and physiologic injury on an individualized level well beyond the capabilities of routine MRI studies. For example, lesions with a more spherical shape and complex surface features demonstrating a positive BOLD slope are metabolically active, suggesting a greater potential for in-situ remyelination. Such findings could not have been achieved with a 2D approach. In addition, the short acquisition time for BOLD slope and minimal degree of post processing required to calculate these outcomes further increases the potential for the disclosed methods, apparatuses, and systems to be clinically adopted in the management of MS patients. Further, the present disclosure provides a platform for disease surveillance as well as quantifying outcomes involving therapeutics aimed at myelin repair.

Referring now to the drawings, FIG. 1 depicts an exemplary 3D imaging and brain lesion representation system 100 according to an embodiment of the disclosure. In the embodiment shown, an MRI device 102 may be provided. The MRI device 102 may be a 2D MRI device, a 3D MRI device, or one or more MRI devices providing both 2D and 3D imaging capabilities. A processing device 104 may be capable of receiving 2D and/or 3D images taken by the MRI device. Processing device 104 may be a part of a computer system that may include standard components such as a hard drive, monitor, printer, keyboard, and mouse, among others, that may enable a user to interact with the processing device 104. In the embodiment shown, processing device 104 may include one or more of a segmentation application 106, a 3D imaging application 108, and one or more databases 110. In some embodiments, segmentation application 106 may be configured to receive one or more MRI images from MRI device 102, segment the one or more MRI images into one or more regions, and enable a selection of one or more regions. These selected regions may be referred to as regions of interest (ROI). In some embodiments, the selection of ROI may be done automatically by processing device 104. In some embodiments, the selection of ROI may be done by a user.

In some embodiments, the selected ROI may be exported by segmentation application 106 and imported into 3D image application 108. In some embodiments, 3D image application 108 may generate one or more 3D maximum intensity projections (MIP) images of the selected ROI. In some embodiments, the selected ROI may correspond to one or more focal brain lesions. In some embodiments, the selected ROI may be converted to stereolithography (.stl) format and/or displayed as 3D orthographic images to enable orthographic views. The one or more 3D images may be displayed to a user and 3D image application 108 may enable a user to view and manipulate the one or more 3D images. In some embodiments, image manipulation capabilities may include capabilities to rotate, zoom, mark, color, and select the one or more images. In some embodiments, one or more databases 110 may contain information corresponding to various brain lesion characteristics. Examples of these brain lesion characteristics may include shape or geometric characteristics, size characteristics, topographical characteristics, volume characteristics, surface area characteristics and the like. In some embodiments, the brain lesion characteristics may be associated with one or more etiologies. Examples of these etiologies may include MS, aging, small vessel disease, migraine headaches, and other non-specific white matter lesion etiologies.

In the embodiment shown, processing device 104 may be configured to send data corresponding to the one or more 3D images to a 3D printing device 112. 3D printing device 112 may create a 3D physical representation of the received one or more 3D images.

FIG. 2 depicts an exemplary method 200 for creating 3D representations of brain lesions according to an embodiment of the disclosure. In one embodiment of the disclosure, method 200 may be implemented by system 100. In the embodiment shown in FIG. 2, method 200 may begin at step 204 by receiving one or more 2D and/or 3D MRI images. In some embodiments, 3D MRI images may be created from one or more received 2D MRI images. Method 200 may continue at step 208 by segmenting the received one or more 2D and/or 3D MRI images. In some embodiments, segmenting step 208 may include segmenting the one or more 2D and/or 3D MRI images into one or more regions of interest (ROI). The one or more ROI may correspond to one or more brain lesions. In some embodiments, brain lesions may be segmented in 3D format using a maximum intensity projection (MIP) 3D file. In this way, the computer system and/or a user may manipulate a 3D object in 2D space and may select one or more ROI. Isolating lesions from 3D MRI images may allow for a better appreciation of both the geometric and surface characteristics of brain lesions. In a 2D view, a variety of signals may influence pixel intensities that may result in pixel misclassification. Isolating lesions from 3D images may overcome some of these shortcomings of 2D lesion isolation.

Method 200 may continue at step 212 by creating one or more 3D models of brain lesions. In some embodiments, the one or more 3D brain lesion models may be orthographic images or MIP images. Method 200 may continue at step 216 by analyzing of one or more 3D phenotypic characteristics of the brain lesion and a slope of a blood oxygen dependent (BOLD) signal from the brain lesion through one or more enlarged boundaries surrounding the brain lesion. For example, a computer system may analyze the one or more brain lesion images to determine one or more characteristics of the brain lesion. A user may also analyze the one or more brain lesion images by interacting with the computer system. In some embodiments, metadata may be used to denote a type or category of a brain lesion characteristic. In some embodiments, brain lesion characteristics may include geometric characteristics. Geometric characteristics may provide insights into a size and shape of a brain lesion. Examples of geometric characteristics may include lesion symmetry/asymmetry, surface morphology (e.g., amorphous, ovoid), the existence of lobes and/or protrusions, and other shape characteristics (e.g., tapered/wedge, spherocylindrical). In some embodiments, brain lesion characteristics may include surface characteristics. Surface characteristics may provide insights into lesion surface traits and lesion properties not associated with geometry. Examples of surface characteristics may include the existence of surface microstructures, surface topography (e.g., steepness/sheerness of surface peaks and valleys), surface irregularities, and a non-uniform distribution of mass of the lesion. In some embodiments, the computer system may engage in machine learning to generate descriptive surface, shape, and signal characteristics from the entire lesion or sections within lesions in order to more efficiently and accurately classify lesion types.

Method 200 may continue at step 220 by determining indicators of one or more brain lesion characteristics. In some embodiments, a computer system may compare the one or more brain lesion characteristics to one or more previously stored brain lesion characteristics to determine possible matches. In some embodiments, one or more previously stored brain lesion characteristics may correspond to one or more brain lesion etiologies. In instances where the analyzed one or more brain lesion characteristics match one or more previously stored brain lesion characteristics, the computer system may determine one or more possible etiologies of the one or more brain lesions. In some embodiments, a user may be able to determine one or more possible etiologies of the one or more brain lesions based on each of their one or more brain lesions characteristics.

A. Experimental Results

Multimodal neuroimaging methods coupled with novel lesion-phenotyping methods were used to study the relationship between lesion 3D shape and texture and the metabolic and physiologic profiles from within and around lesions in one or more enlarged boundaries (e.g., concentric perimeters) in multiple sclerosis (MS) patients. Lesion phenotyping and physiologic characterization allowed the study of the impact of lesions on surrounding tissue and identification of lesion characteristics within and around lesion tissue, resulting in identification of an association of lesions' shapes and surface features with their metabolic signatures. Such associations aid in the prospect for immediate translation of 3D MRI data to clinical management by providing information related to metabolic activity, lesion age, and risk for disease reactivation and self-repair. Further, the disclosed methods, apparatuses, and systems provide a platform for disease surveillance and outcome quantification involving therapeutics aimed at myelin repair.

1. Participants

A study cohort was comprised of 23 relapsing-remitting MS patients (female=17 (74%); median age=55 years (range=29-61)), and median disease duration=11 years (range=1-30). A total of 109 MS lesions and 27 simulated lesions created from 4 age- and sex-matched healthy control (HC) brains were studied. The simulated lesions in HC brains were location-matched to focal lesions in MS patient brains. Table 1 below summarizes the baseline demographic and clinical data from the study cohort.

TABLE 1

| Characteristics | MS patients (N = 23) |
|---|---|
| Age (years) Median (range) | 55 (29-61) |
| Female sex No. (%) | 17 (74%) |
| Disease duration (years) Median (range) | 11 (1-30) |
| Patients on disease modifying therapy No. (%) | 16 (69.6%) |
| Age at diagnosis (years) Median (range) | 38 (26-54) |
| Time since last acute exacerbation (years) Median (range) | 2.8 (0.4-13.3) |
| EDSS score Median (range) | 2.5 (1-7.5) |
| Total lesion volume Median (range) | 3.035 (0.12-26.32) |

Figure 3A:
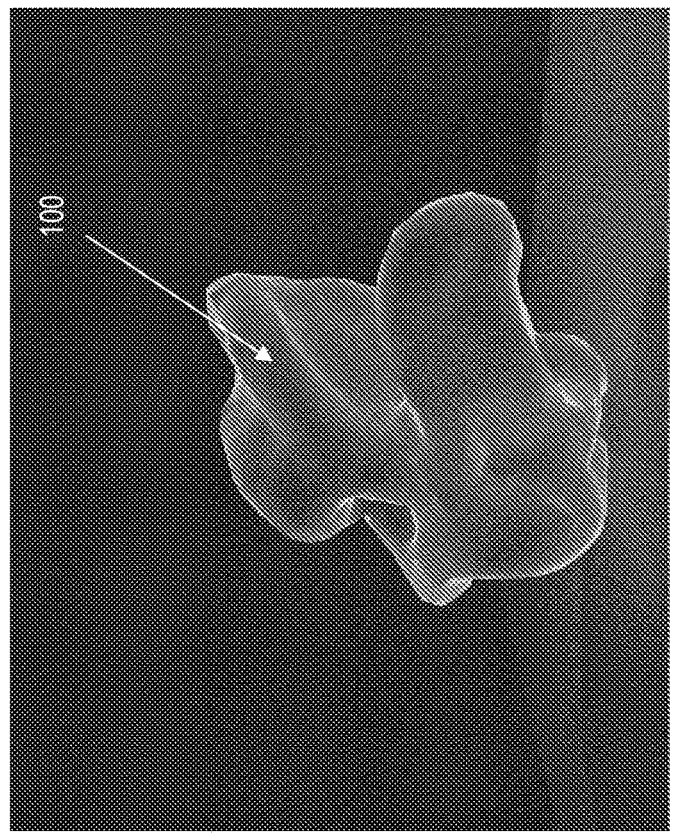
FIG. 3A shows a three-dimensional representation of a multiple sclerosis (MS) brain lesion isolated in 3D using geodesic active contours.

Referring now to FIGS. 1A-1B, in some implementations the physiology around a multiple sclerosis (MS) brain lesion 100 was studied in one or more enlarged boundaries (e.g., concentric 3 mm layers in 3D) surrounding the brain lesion. As best shown in FIG. 3A, an exemplary MS brain lesion 100 and its perimeters can be represented in 3D using geodesic active contour methodology. In some implementations, the layer immediately adjacent to the lesion may be designated as Perimeter 1 and each layer extending out from perimeter 1 may be sequentially numbered as Perimeters 2-4. As shown in FIG. 3B, exemplary MS brain lesion 100 has a Perimeter 1 (104) and a Perimeter 2 (108), but can also have one or more additional perimeters associated with the brain lesion.

In some implementations, to test whether the physiologic influences of a lesion on its surrounding tissue were lesion-specific, blood oxygen level dependent (BOLD) signal and cerebral blood flow (CBF) was compared in focal lesions and their surrounding perimeters in MS patients to BOLD signal and CBF in simulated lesions and their perimeters in healthy controls (HCs). To account for individual differences in BOLD signal and CBF, average values in lesions and their perimeters were normalized to their respective grey matter values.

Figure 4A:
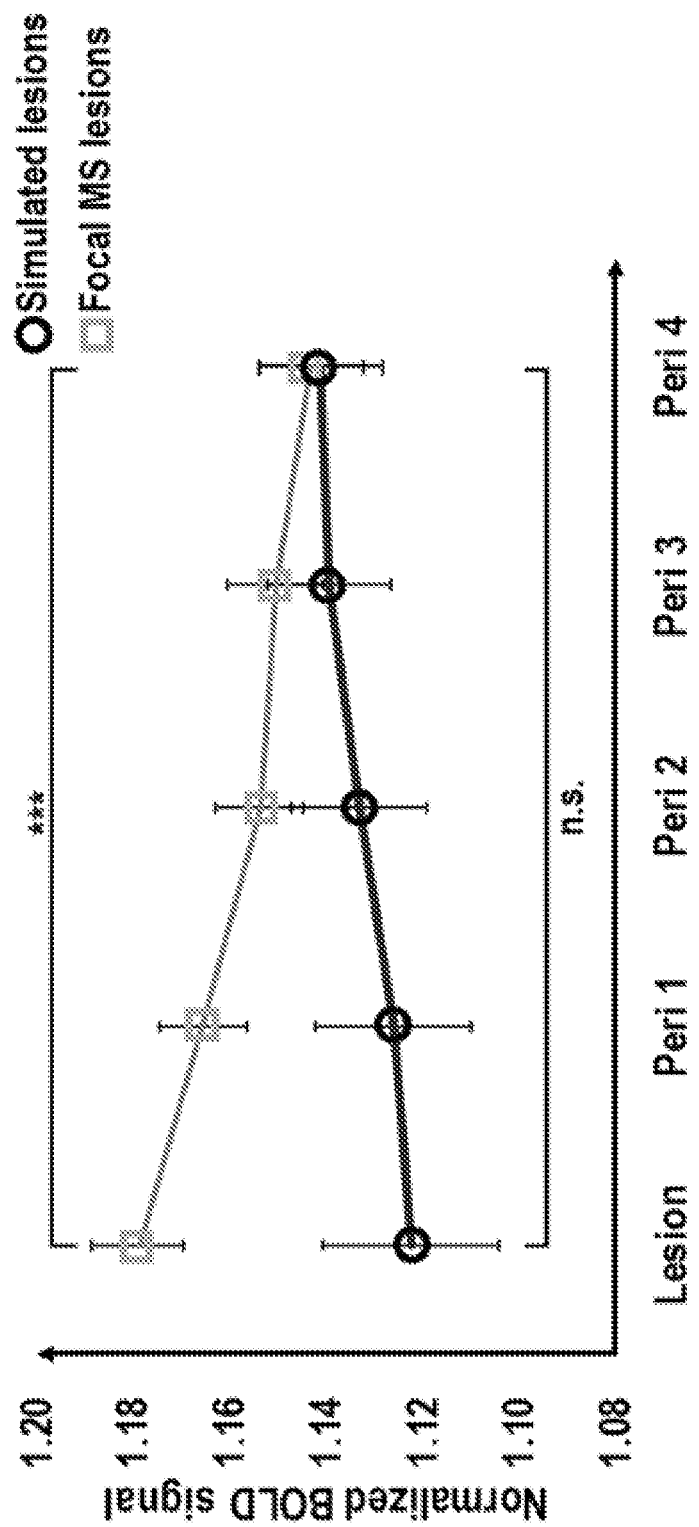
FIG. 4A shows the mean normalized blood oxygen level dependent (BOLD) signal in MS brain lesions and their associated Perimeters 1-4 (Peri) in focal MS (denoted as solid line with squares in the graph) and simulated MS brain lesions (denoted as solid line with triangles in the graph).

In some implementations, alterations in the blood oxygenation of surrounding brain tissue was observed in the one or more enlarged boundaries (e.g., concentric perimeters) surrounding focal MS lesions. It was determined that MS lesions alter surrounding tissue blood oxygenation without altering blood flow. As shown in FIG. 4A, focal MS lesions showed sequential reductions in BOLD signal from the lesion center outward to the perimeters ($F(1.234, 133.243)=17.222$, $p<0.0005$, partial $\eta2=0.138$). Simulated lesions showed no such differences ($F(1.122, 29.160)=2.088$, $p<0.158$). There were significant differences in BOLD signal between focal MS lesions and simulated lesions ($M_{MS}=1.18$, $SD_{MS}=0.097$, $M_{HC}=1.12$, $SD_{HC}=0.094$, $F(1, 134)=7.351$, $p<0.008$, partial $\eta2=0.052$) and perimeter 1 ($M_{MS}=0.17$, $SD_{MS}=0.092$, $M_{HC}=1.13$, $SD_{HC}=0.084$, $F(1, 134)=4.065$, $p<0.05$). There were no differences between focal and simulated lesions in perimeters 2, 3 and 4. Statistical analyses revealed a significant interaction between lesion types (focal versus simulated lesions) and brain regions (lesion and its perimeters), $F(1.225, 162.258)=8.942$, $p<0.002$, partial $\eta2=0.063$. Statistics were obtained using a two-way mixed ANOVA model. All p-values were corrected for multiple comparisons in the model using Bonferroni methods (*, , *=$p<0.05, 0.005, 0.0005$).

Figure 4B:
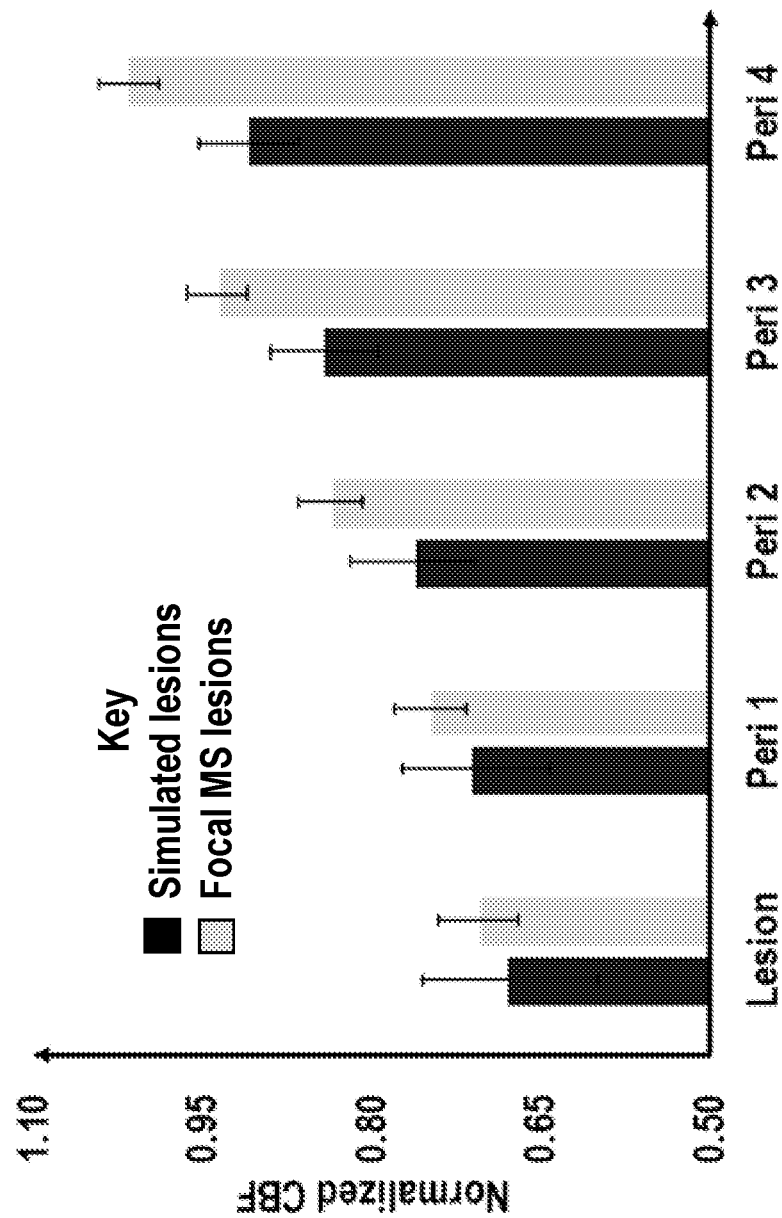
FIG. 4B shows the mean normalized cerebral blood flow (CBF) in lesions and their associated Perimeters 1-4 in focal MS and simulated MS brain lesions.

As shown in FIG. 4B, the mean normalized cerebral blood flow (CBF) in lesions and their associated Perimeters 1-4 in focal MS and simulated MS brain lesions were determined. There were no significant differences in CBF between focal MS brain lesions and simulated MS brain lesions in all regions. Statistical analysis revealed no significant interaction between lesion types and brain regions ($p<0.471$).

In some implementations, plotting the mean BOLD signal in 109 MS lesions and surrounding Perimeters 1-4 indicated two characteristic types of lesions: (i) those with a decreasing trend, or (ii) those with a similar or increasing trend in BOLD signal from each lesion to its perimeters. The BOLD slope was calculated as the change in BOLD signal from each focal lesion to its associated Perimeters 1-4. It was determined that the BOLD slope distinguishes these two characteristic lesion types.

Figure 5A:
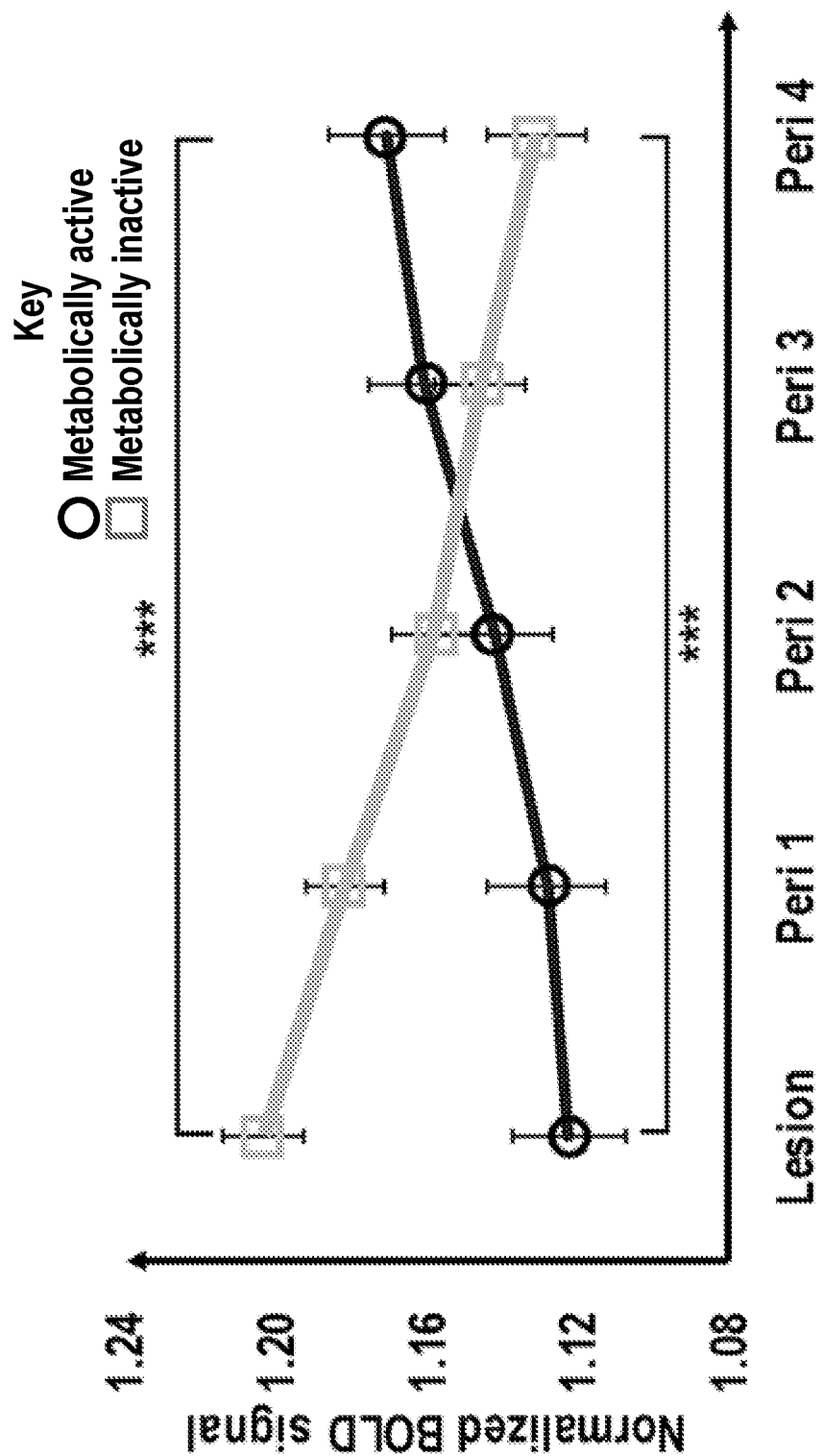
FIG. 5A shows the mean normalized BOLD signal in the MS brain lesions and their Perimeters (Peri) 1-4 for metabolically active (solid line with squares) and inactive lesions (solid line with triangles).
Figure 5B:
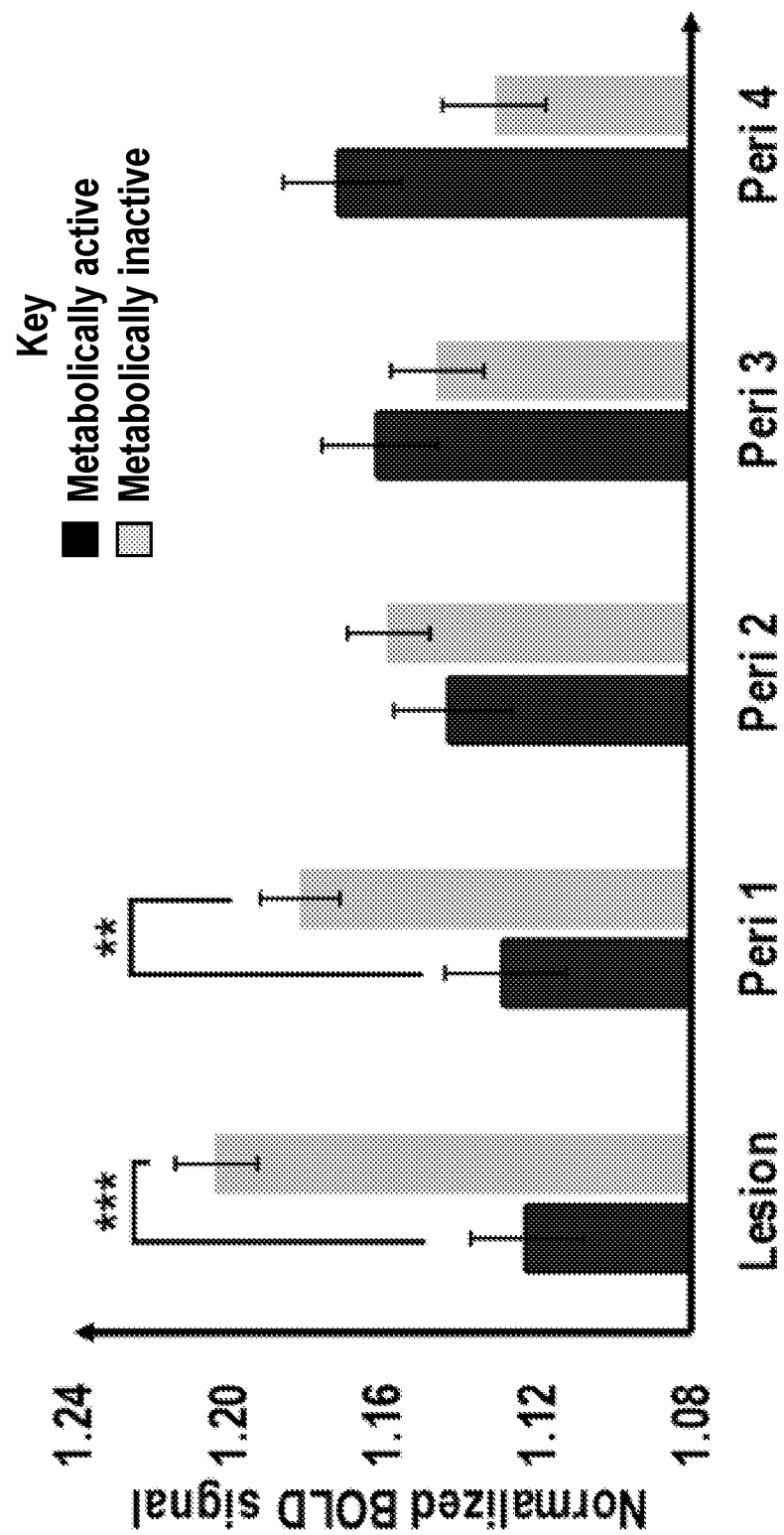
FIG. 5B shows the significant differences in BOLD signal between positive and negative BOLD slope MS brain lesion types.

In some implementations, to test the hypothesis that the BOLD signal significantly changes from each lesion to its perimeter, two-way mixed ANOVA was performed, described in further detail below. As shown in FIG. 5A, positive BOLD slope lesions (nMA=33) had significantly increasing BOLD signal from lesions to their perimeters ($F(1.563, 50.002)=57.040$, $p<0.0005$, partial $\eta2=0.641$, depicted as solid line with black circles). Negative BOLD slope lesions (nMI=76) had significantly decreasing BOLD signal from lesions to their perimeters ($F(1.354, 101.548)=65.324$, $p<0.0005$, partial $\eta2=0.466$, depicted as solid grey line with squares). As shown in FIG. 5B, in some implementations there were significant differences in BOLD signal between positive and negative BOLD slope lesion types in the lesion tissue ($M_{MA}=1.12$, $SD_{MA}=0.085$, $M_{MI}=1.20$, $SD_{MI}=0.092$, $F(1, 107)=18.406$, $p<0.0005$, partial $\eta2=0.147$) and Perimeter 1 ($M_{MA}=1.13$, $SD_{MA}=0.09$, $M_{MI}=1.18$, $SD_{MI}=0.089$, $F(1, 107)=8.102$, $p<0.005$, partial $\eta2=0.070$;). There were no differences between lesion types in Perimeters 2, 3 and 4. Statistics were obtained using a two-way mixed ANOVA model. All p-values were corrected for multiple comparisons in the model using Bonferroni methods (*, , *=$p<0.05, 0.005, 0.0005$).

As summarized in Table 2 below, there were no significant differences in the spatial distribution (classified as juxtacortical, subcortical, deep white matter, periventricular; $p<0.06$) or location (classified as those present in frontal, parietal, temporal or occipital lobe; $p<0.24$) between the two lesion types.

TABLE 2

| Characteristics | | Metabolically active (N = 33) | Metabolically inactive (N = 76) | Statistics |
|---|---|---|---|---|
| Definition | BOLD slope | Positive | Negative | $p < 0.0005$ |
| Lesion location | Frontal lobe | 39.39% | 35.52% | $p < 0.24$ |
| | Temporal lobe | 3.03% | 13.15% | |
| | Parietal lobe | 57.57% | 47.36% | |
| | Occipital lobe | — | 3.9% | |
| Lesion type | Juxtacortical | — | 3.94% | $p < 0.06$ |
| | Subcortical | 39.39% | 28.94% | |
| | Deep white matter | 51.15% | 36.84% | |
| | Periventricular | 9.09% | 30.26% | |
| Physiologic properties | $CMRO_2$ Mean (SD) | 0.69 (0.19) | 0.47 (0.25) | $p < 0.0005$ |
| | CBF Mean (SD) | 0.85 (0.32) | 0.68 (0.39) | $p < 0.03$ |
| Microstructural properties | White matter microstructure like myelin | 0.88 (0.08) | 0.81 (0.09) | $p < 0.0005$ |
| 3D phenotyping | Lesion volume ($cm^3$) Mean (SD) | 1.27 (0.33) | 1.08 (0.31) | $p < 0.005$ |
| | Surface texture | Rough | Smooth | $p < 0.0005$ |
| | Lesion shape | Less complex | More complex | $p < 0.0005$ |

In some implementations, $CMRO_2$, which reflects the amount of cellular oxygen utilization, was calculated from the BOLD signal and CBF in the lesions and their perimeters 1-4 using the deoxyhemoglobin dilution model (see Materials and Methods). Normalized lesion $CMRO_2$ represents $CMRO_2$ in the lesion relative to that in the native brain grey matter. To test the hypothesis that lesions with a positive BOLD slope were metabolically active (nMA=33) and those with a negative BOLD slope were metabolically inactive ($n_{MI}$=76), normalized $CMRO_2$ in each lesion and its perimeters were compared between the two lesion types. It was determined that positive BOLD slope lesions are more metabolically active than negative BOLD slope lesions.

As shown in FIG. 5C, in metabolically inactive lesions, $CMRO_2$ sequentially increased significantly from the lesion to its perimeters $F(1.307, 98.012)=114.181$, $p<0.0005$, partial $\eta2=0.604$). In metabolically active lesions, $CMRO_2$ showed no differences moving from the lesion to its perimeters $F(1.277, 40.87)=2.360$, $p<0.13$, partial $\eta2=0.069$). Statistical analyses revealed a significant interaction in $CMRO_2$ between the lesion types and brain regions, $F(1.308, 139.99)=26.543$, $p<0.0005$, partial $\eta_2=0.199$.

Figure 5D:
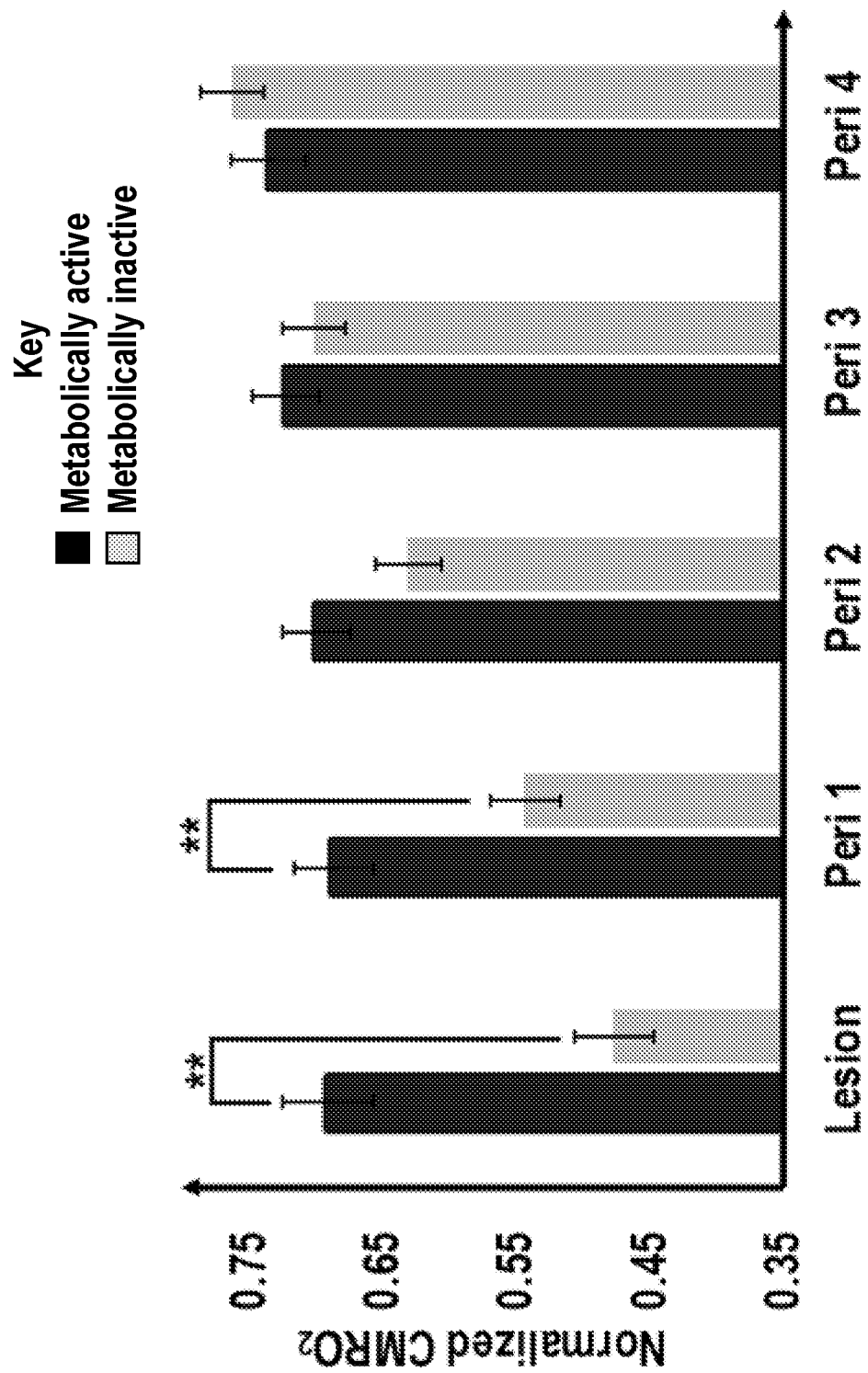
FIG. 5D shows the significant differences in $CMRO_2$ between metabolically active and metabolically inactive MS brain lesion types.

As shown in FIG. 5D, metabolically active lesion type had significantly higher $CMRO_2$ in the lesion tissue ($M_{MA}$=0.69, $SD_{MA}$=0.194, $M_{MI}$=0.47, $SD_{MI}$=0.257, $F(1, 107)=18.217$, $p<0.0005$, partial $\eta2=0.145$), Perimeter 1 ($M_{MA}$=0.69, $SD_{MA}$=0.167, $M_{MI}$=0.54, $SD_{MI}$=0.223, $F(1, 107)=10.891$, $p<0.001$, partial $\eta2=0.092$) than metabolically inactive lesion type. There were no significant differences in $CMRO_2$ between the lesion types in Perimeter 2 ($M_{MA}$=0.70, $SD_{MA}$=0.144, $M_{MI}$=0.63, $SD_{MI}$=0.209, $p<0.08$), Perimeter 3 ($M_{MA}$=0.72, $SD_{MA}$=0.146, $M_{MI}$=0.70, $SD_{MI}$=0.208, $p<0.61$) and Perimeter 4 ($M_{MA}$=0.73, $SD_{MA}$=0.161, $M_{MI}$=0.76, $SD_{MI}$=0.206, $p<0.50$).

Figure 5E:
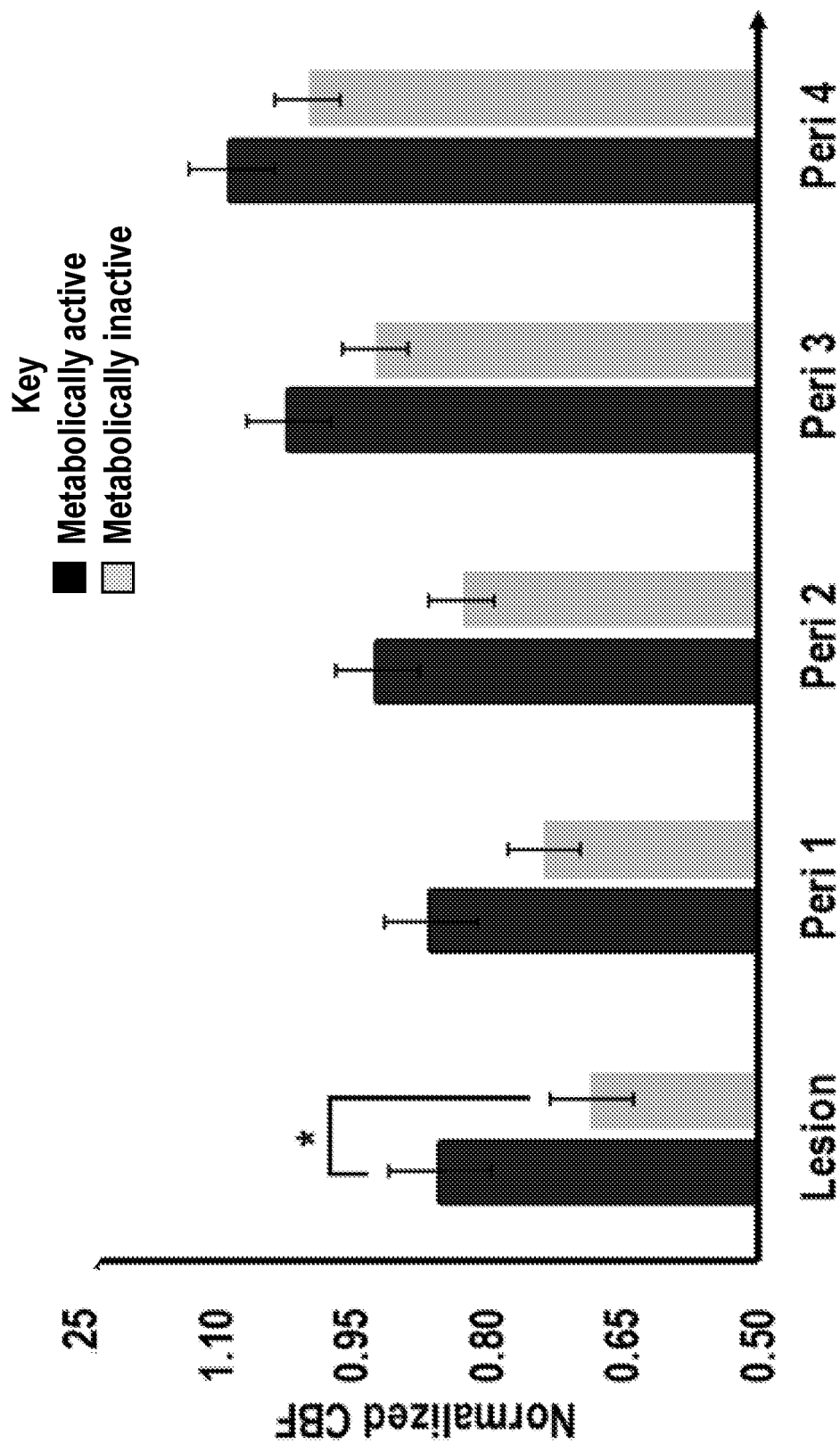
FIG. 5E shows the significantly higher CBF in metabolically active lesions than inactive lesions.

It was hypothesized that metabolically active lesions would have higher CBF than inactive lesions. As shown in FIG. 5E, in some implementations one-way ANOVA revealed significantly higher CBF in metabolically active lesions than inactive lesions ($M_{MA}$=0.85, $SD_{MA}$=0.323, $M_{MI}$=0.68, $SD_{MI}$=0.395, $F(1, 107)=4.590$, $p<0.03$, partial $\eta2=0.04$). There were no differences in CBF between the lesion types in Perimeter 1 ($M_{MA}$=0.86, $SD_{MA}$=0.291, $M_{MI}$=0.736, $SD_{MI}$=0.291, $p<0.07$), Perimeter 2 ($M_{MA}$=0.92, $SD_{MA}$=0.266, $M_{MI}$=0.82, $SD_{MI}$=0.315, $p<0.14$), Perimeter 3 ($M_{MA}$=1.01, $SD_{MA}$=0.267, $M_{MI}$=0.923, $SD_{MI}$=0.315, $p<0.13$), and Perimeter 4 ($M_{MA}$=1.08, $SD_{MA}$=0.278, $M_{MI}$=0.99, $SD_{MI}$=0.319, $p<0.19$). Thus, it was determined that metabolically active lesions have higher blood flow than inactive lesions.

Figure 5F:
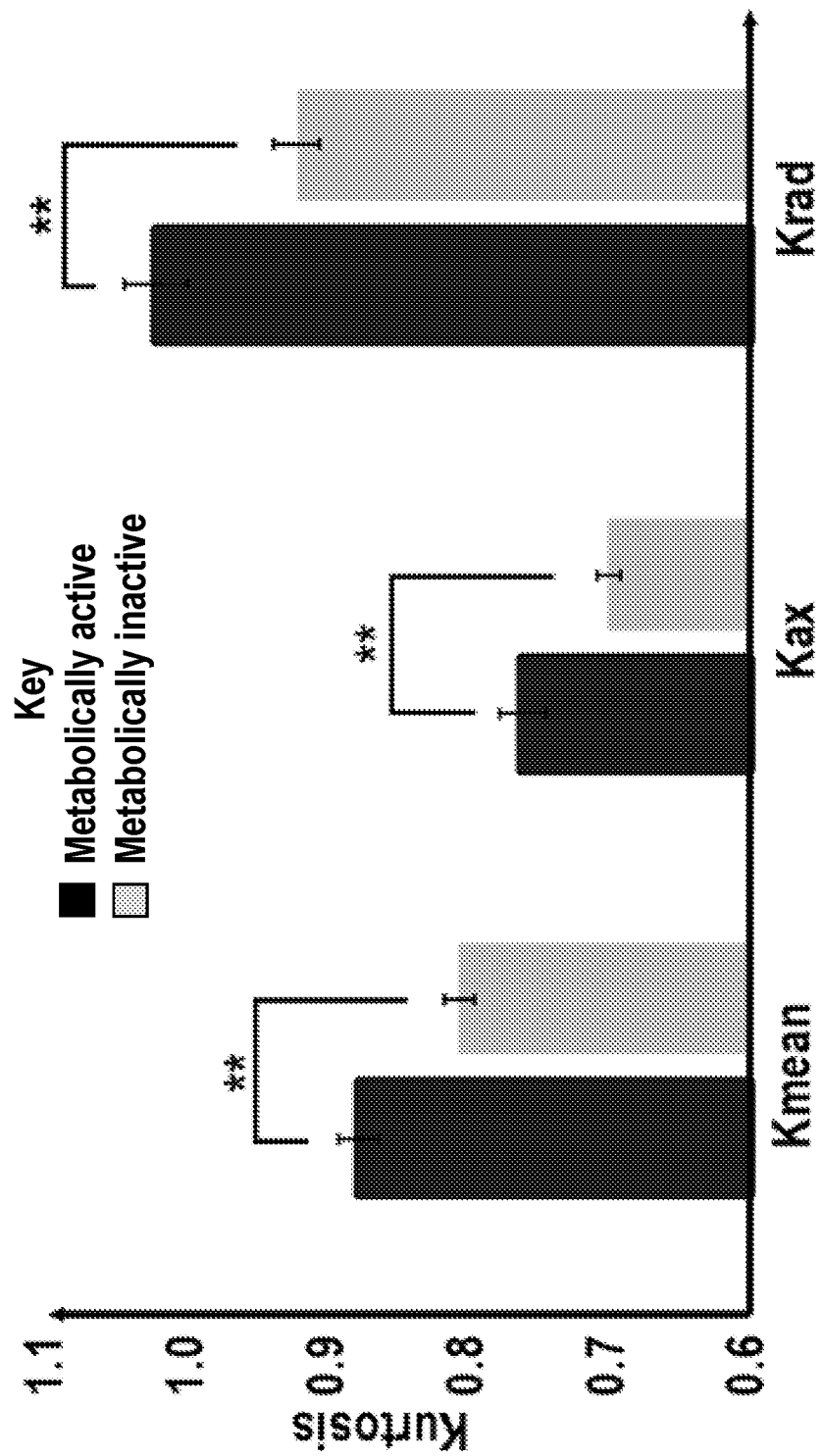
FIG. 5F depicts the significant presence of more intact white matter microstructure (e.g., myelin) in metabolically active lesions compared to inactive lesions as measured by presence of kurtosis tensors.

In some implementations, the intactness of the underlying white matter microstructure like myelin was assessed using diffusion kurtosis tensors. It was determined that metabolically active lesions have more intact white matter microstructure than inactive lesions. As shown in FIG. 5F, mean kurtosis (Korean) was significantly higher in metabolically active lesions (M=0.88, SD=0.085) than metabolically inactive lesions (M=0.81, SD=0.098), $t(107)=3.626$, $p<0.0005$. Axial kurtosis ($K_{ax}$) and radial kurtosis ($K_{rad}$) was significantly higher in metabolically active lesions ($M_{ax}$=0.76, $SD_{ax}$=0.098, $M_{rad}$=1.02, $SD_{rad}$=0.128) than metabolically inactive lesions ($M_{ax}$=0.70, $SD_{ax}$=0.072, $M_{rad}$=0.923, $SD_{rad}$=0.144; $t_{ax}(107)=3.619$, $p_{ax}<0.0005$, $t_{rad}(107)=3.476$, $p_{rad}<0.001$). Presence of higher kurtosis tensors in metabolically active than inactive lesions indicated the presence of more intact white matter microstructure like myelin in metabolically active lesions compared to inactive lesions.

Referring now to FIG. 6A, examples of metabolically inactive (e.g., 112a, 112b, 112c) and active (e.g., 116a, 116b, 116c) MS brain lesions in 2D and 3D views (e.g., 112d, 116d) demonstrating the marked underrepresentation of the MS brain lesion shape and texture in 2D forced perspectives of MRI. As shown in FIG. 6A, in some implementations a significant difference in surface complexity between metabolically active lesions 116d and inactive lesions 112d was observed. It was determined that metabolically active lesions have more complex surface features than inactive lesions. As best depicted in FIG. 6D, higher surface area-to-volume ratios were demonstrated in metabolically active lesions ($M_{MA}$=1.27 cm-1, $SD_{MA}$=0.335) as compared to inactive lesions ($M_{MI}$=1.08 cm-1, $SD_{MI}$=0.31), $t(107)=2.888$, $p<0.005$).

Figure 6B:
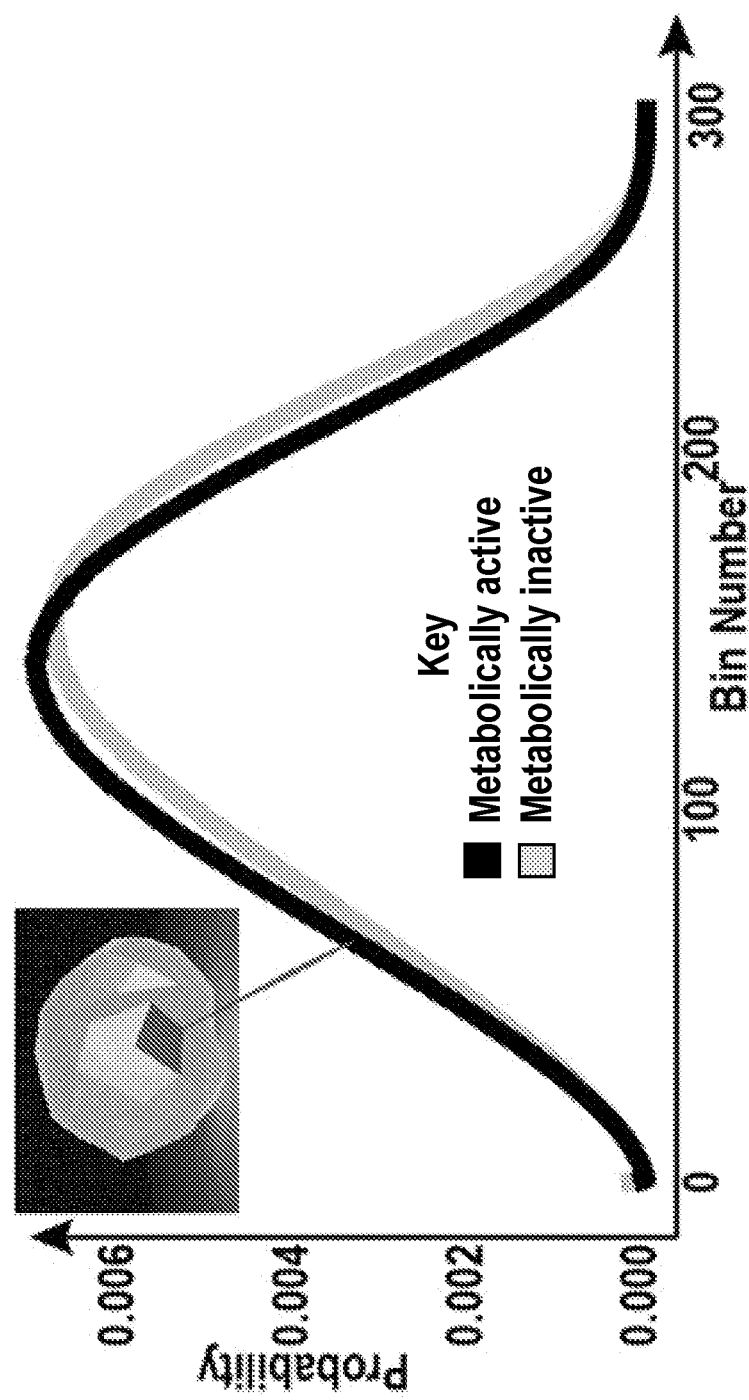
FIG. 6B shows the probability density functions of the two lesion types, metabolically active (solid black line) and inactive (solid grey line), obtained from bootstrapping the cube root of randomly sampled $1 \times 10^6$ tetrahedron areas on the lesion surface.

As best depicted in FIGS. 6A-6B, to evaluate specifically for the presence of unique surface features between groups, probability distributions of the cube root of the tetrahedron area were obtained by randomly sampling $1 \times 10^6$ tetrahedrons from the surface of each lesion. L2-norm-based bootstrap test was used to test for differences in the probability distribution between the two lesion types. The difference in these functions was significant ($p<0.0001$). As shown in FIG. 6B, the test demonstrated significant differences in the probability distribution between metabolically active and inactive lesions, Tn=29.1, $p<0.0001$. Such differences indicated that metabolically active lesions have more complex surface features than metabolically inactive lesion.

Figure 6C:
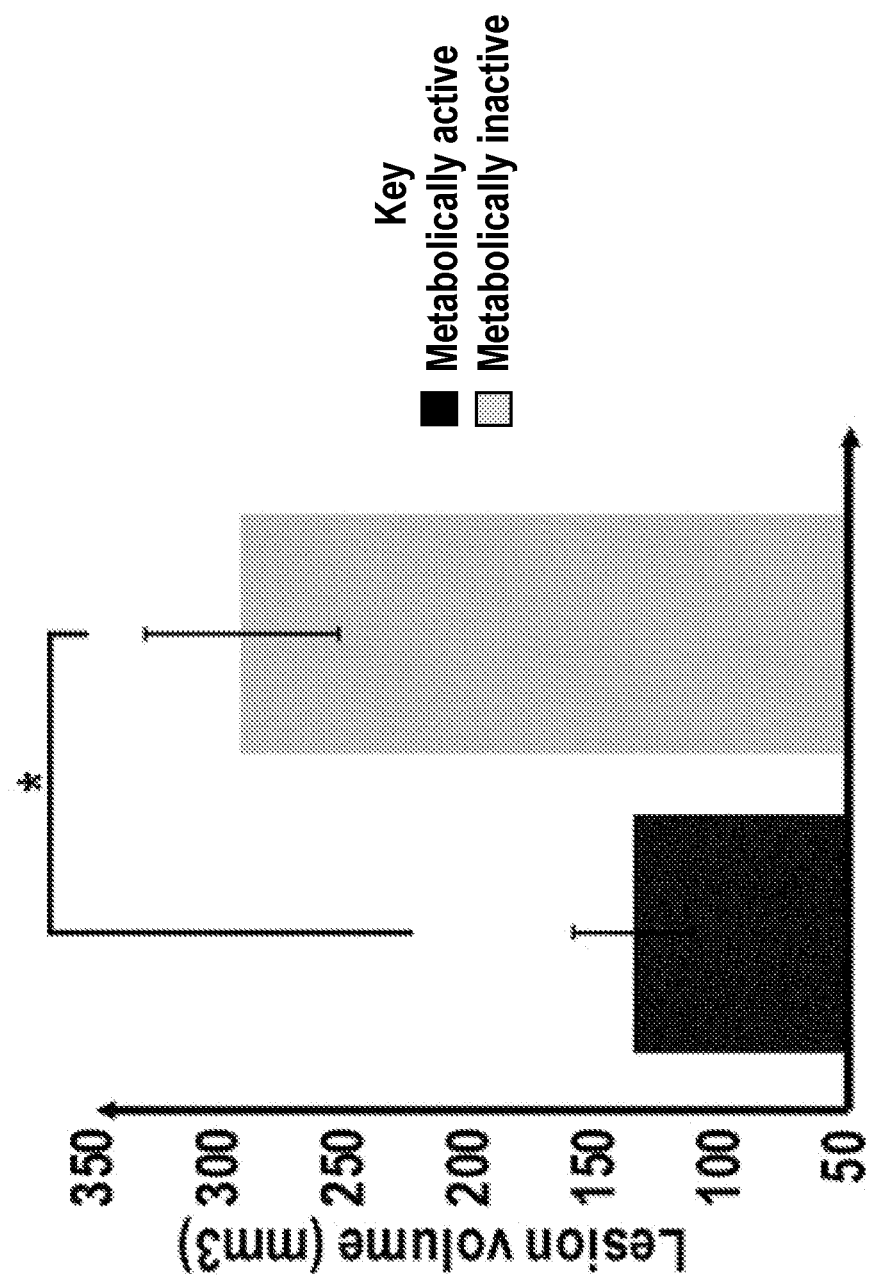
FIG. 6C depicts a bar graph showing mean lesion volumes of the two lesion types.
Figure 6D:
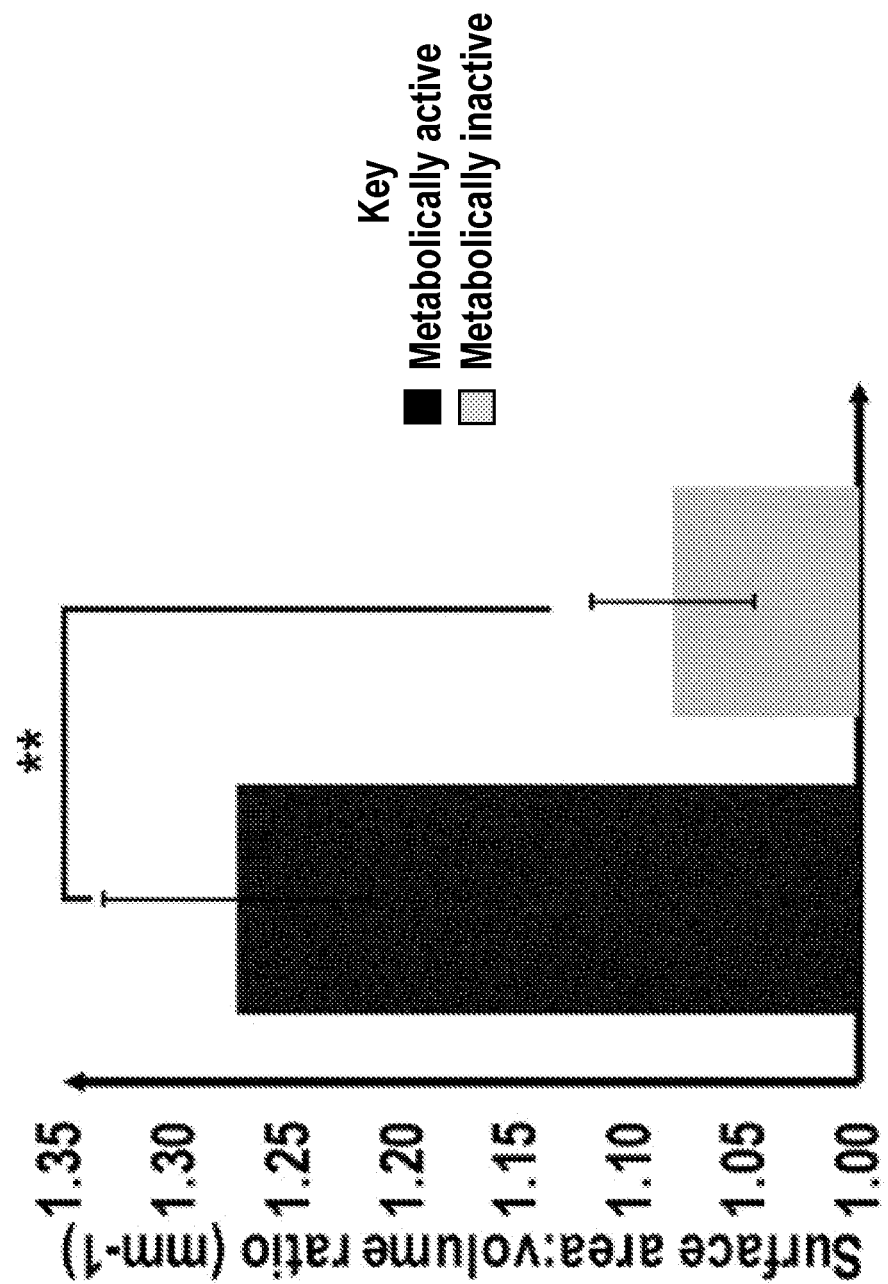
FIG. 6D depicts a bar graph showing mean surface area-to-volume ratio for the two lesion types.
Figure 6E:
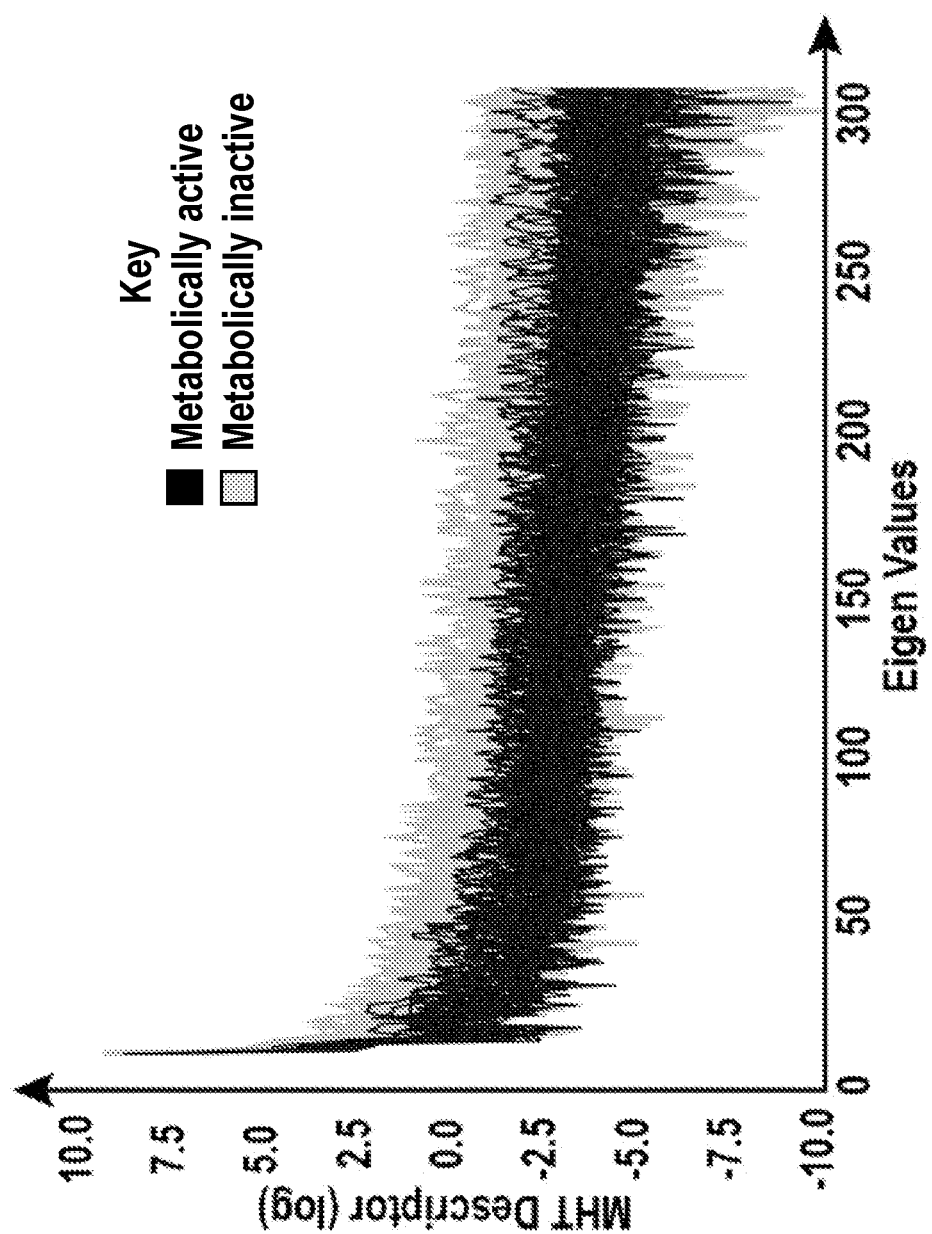
FIG. 6E shows Log transformed manifold harmonics transform (MHT) descriptors plotted as a function of their eigenvalues for each lesion.

In some implementations, the volume differences between metabolically active and inactive lesions were compared. It was determined that metabolically active lesions are smaller and less complex in shape than inactive lesions. As shown in FIG. 6C, metabolically active lesions ($M_{MA}$=135.62 $mm^3$, $SD_{MA}$=133.99 $mm^3$) were significantly smaller than metabolically inactive lesions ($M_{MI}$=291.59 $mm^3$, $SD_{MI}$=338.59 $mm^3$; $t(106.4)=-3.443$, $p<0.001$). In some implementations, manifold harmonics transforms (MHT) were used to assess for shape differences between lesion groups with varying metabolic activity. As shown in FIG. 6E, metabolically inactive lesions (shown in grey) demonstrated increased higher frequency characteristics suggesting greater variation from a symmetric shape compared to metabolically active lesions (shown in black).

Figure 6F:
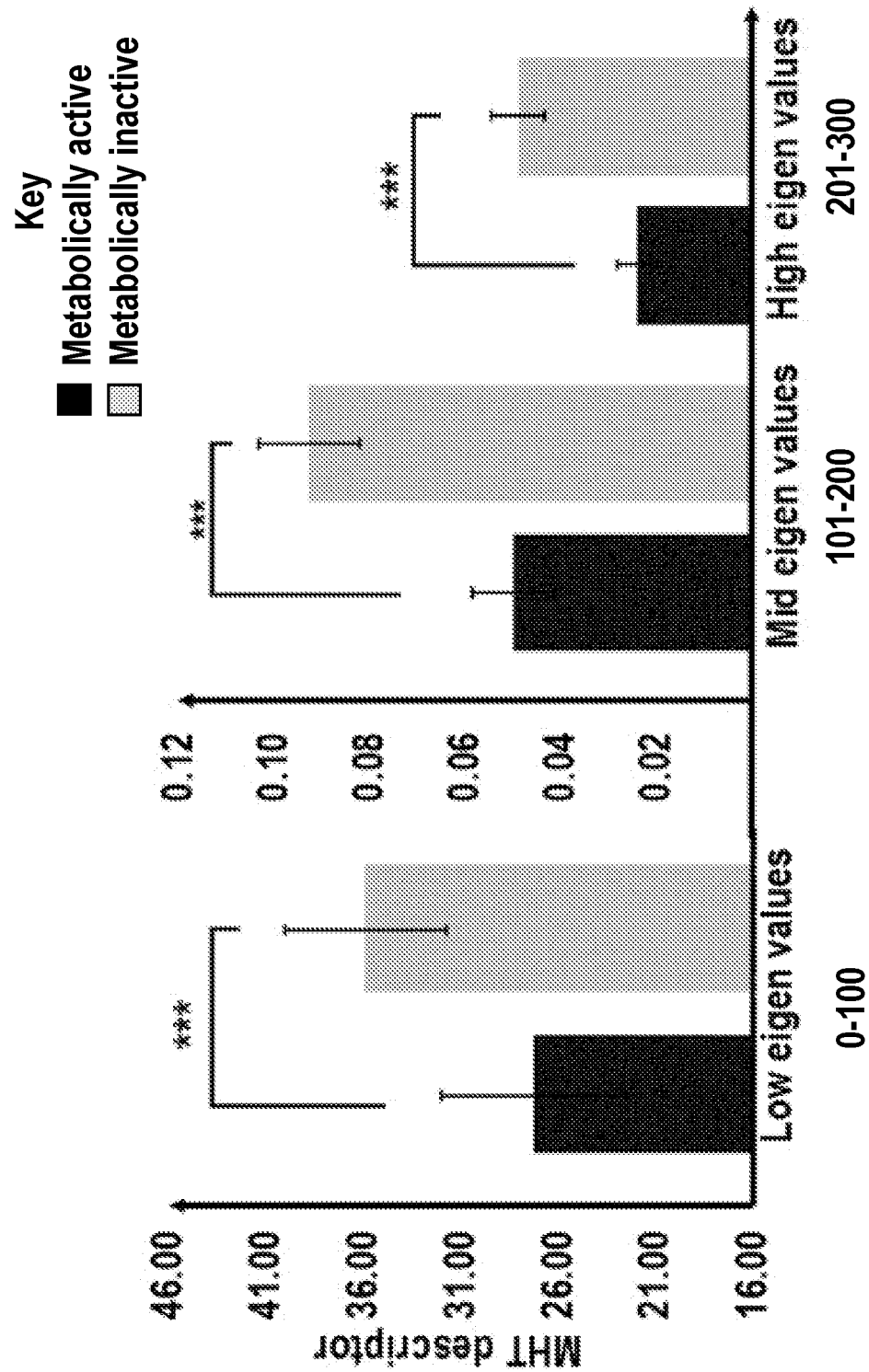
FIG. 6F depicts bar graphs showing mean MHT descriptors of low (0-100), mid (101-200) and high (201-300) eigenvalues for the two lesion types.

As shown in FIG. 6F, low frequency eigenvalues (1-100) with features supportive of dynamic shapes, manifold harmonics transform (MHT) descriptors were significantly greater for metabolically inactive lesions relative to metabolically active lesions (p<0.0001; TA=10.489, df1=2.342, df2=210.1358). Similarly, for mid frequency (101-200; p<0.0001; TA=8.259, df1=2.664, df2=239.0421), and high frequency (201-300) eigenvalues (p<0.0001; TA=9.728, df1=2.683, df2=240.7007), associated with shapes deviating from shape symmetry, MHT descriptors were significantly greater for metabolically inactive lesions relative to active lesions.

In some implementations of the present methods, a non-invasive biomarker, BOLD slope, was identified through a novel technique of assessing physiologic data from the lesion tissue and one or more enlarged boundaries (e.g., surrounding concentric perimeters) extending from the surface of a 3D MS lesion. Obtaining the BOLD slope can be used to clinically characterize metabolism in and around lesions. In some implementations, as shown in Table 2, lesions with a positive BOLD slope are metabolically active and are associated with (1) increased CBF, (2) more intact white matter microstructure like myelin (3) more complex surface texture, and, (4) less complex shape features than metabolically inactive lesions. In some implementations, the association of lesion shape and surface features with its metabolic signatures suggest the prospect for immediate translation of MRI data to clinical management by providing information related to metabolic activity.

Focal injury to brain tissue resulting from MS is associated with demyelinating lesions that are metabolically heterogeneous. Currently, the clinical management of MS patients is limited by 2D forced perspectives of MRI views that markedly underrepresents the complexity of lesion shape and texture. Observations made from the 2D perspective fail to appreciate the magnitude of injury within and around MS lesions, the extent of alterations in the underlying metabolism, the potential for self-remyelination and recovery, and the long-term outcomes related to the impact of lesions on their surrounding brain tissue.

In some implementations, the inclusion of a lesion-isolation technique enabled the direct extraction of lesions in 3D without reconstruction through 2D slices and allowed for lesion traits to be phenotyped. In this way, the findings indicate that specific 3D lesion traits may inform the underlying physiology in the lesion tissue and the surrounding brain parenchyma. For example, more complex surface textures were observed in metabolically active lesions than inactive lesions. Additionally, lesion texture complexity might result from cellular activity related to inflammation and tissue remodeling in and around MS lesions. Acute lesions feature increased cellular activity compared to chronic lesions. Histopathological studies have previously demonstrated that acute lesions are associated with irregular lesion borders compared to chronic lesions. The results show that irregular lesion borders in metabolically active lesions are apparent as complex surface texture when viewed using 3D MRI. As remyelination is more robust in active than inactive lesions, alterations in lesion surface texture might reflect the greater potential of new lesions to undergo myelin repair compared to older lesions.

Beyond differences in surface texture between lesion types, shape differences were also identified. Lesions with greater metabolic activity were found to be less complex in shape, having more spherical and symmetrical characteristics when compared to metabolically inactive lesions. This finding might be a reflection of differences in lesion vascularity, lesion age, and extent of myelination, between the two lesion types. The results indicate that acute, metabolically active lesions have smaller volumes, and limited shape complexities, as well as complex surface features, compared to inactive lesions. Such newly formed lesions would be expected to have lower volumes and limited shape complexities when compared to existing lesions. Newer lesions would also have an increased potential for disease reactivation, enlargement over time, and self-repair. Chronic, metabolically inactive lesions have larger volumes, more shape complexities, and less complex surface features compared to active lesions. Such older lesions would be expected to have higher volumes and more shape complexities due to the reduced edema surrounding chronic lesions, gliosis, and alterations in the surrounding brain parenchyma resulting from MS-related secondary degenerative changes.

The extent of metabolism in and around MS lesions appears to reflect the impact of focal MS lesions on their surrounding brain tissue, microscopic inflammation near the lesion borders, or the physiologic response to MS-related injury, and mediators of myelin repair. Consistent with the presently disclosed classification of lesions as metabolically active or inactive, immunopathology on demyelinating MS lesions in humans extending from lesion center to the periphery have identified two characteristic lesion types by the detection of elevated intra-versus extra-lesional oligodendrocyte number. Thus, metabolic activity in lesion tissue may reflect oligodendrocyte activity, and therefore, a greater capacity to remyelinate when compared to inactive lesions with fewer oligodendrocytes.

The metabolic impact of lesions on adjacent tissue may be an important contributor to the heterogeneity observed in MS-related injury. Tissue within MS lesions are subjected to a virtual hypoxic state caused by an imbalance between energy demand and supply. This hypoxic state may be due to impaired mitochondrial energy production, reductions in CBF itself, or a combination of these factors. It was observed that MS lesions impair surrounding venous blood oxygenation without altering arterial blood flow. This observation suggested that the impaired venous oxygenation was mediated by the diversity and activity of cells within and around lesions.

The cellular diversity in and around MS lesions drive physiologic processes. Such diversity is reflected in the metabolism within and around lesions. Metabolically active lesions demonstrated higher $CMRO_2$ compared to metabolically-inactive lesions. Rates of de- and remyelination vary based on lesion age and are impacted by enzymatic mechanisms following oxidative stress and hypoxic injury. Myelin biosynthesis is a metabolically demanding process. This process requires mitochondrial oxidative phosphorylation for ATP production (high $CMRO_2$) and glycolysis to provide the substrates needed for myelination. These dynamic factors are significant in affecting the lesion shape and surface characteristics and its associated surrounding brain tissue.

The present disclosure shows that there is evidence for two lesion types distinguished by shape and surface texture. Smaller acute lesions with rough surface textures, are characterized by an abundance of repair-related metabolic activity which, if supported by myelin-repair therapies, could improve or resolve over time. Larger chronic lesions with smoother textures are characterized by a paucity of repair-related metabolic activity would be expected to remain static over time. The results suggest that studying lesion metabolism along with their 3D shape and texture informs the capacity for remyelination.

The 3D approach to the study of MS lesion phenotype offers a more accurate reflection of the underlying microstructural and physiologic injury on an individualized level well beyond the capabilities of routine MRI studies. Lesions with a more spherical shape and complex surface features demonstrating a positive BOLD slope are metabolically active, suggesting a greater potential for in-situ remyelination. Such findings could not have been achieved with a 2D approach. In addition, the short acquisition time for BOLD slope and minimal degree of post processing required to calculate these outcomes further increases its potential in the clinical management of MS patients. The findings provide a platform not only for disease surveillance but for quantifying outcomes involving therapeutics aimed at myelin repair.

B. Materials and Methods

1. Research Participants

The study group was ascertained from patients evaluated in the Clinical Center for Multiple Sclerosis at the University of Texas Southwestern (UTSW) Medical Center and from nearby MS support groups. HCs were recruited in the Dallas-Fort Worth Metroplex area. Inclusion criteria were comprised of (i) male or female patients between the ages of 18 and 65 with (ii) a confirmed diagnosis of a relapsing-remitting disease course based on 2010 McDonald criteria having (iii) an Expanded Disability Status Scale (EDSS) score less than 7.5. Patients were also required to be (iv) clinically stable on disease modifying therapy or (v) treatments for comorbid psychiatric illness (i.e., depression, generalized anxiety disorder), if present, for at least 90 days, (vi) at least 30 days past their most recent clinical exacerbation and (vii) exposure to their last glucocorticosteroid treatment. Exclusion criteria included (i) left-handed patients, (ii) pregnant or nursing women, (iii) history of smoking or cardiopulmonary illness due to the use of carbogen (5% $CO_2$ and 95% room air), and (iv) contraindications to MRI scanning.

2. MRI Data Acquisition

The study was approved by the University of Texas Southwestern Medical Center Institutional Review Board. Informed written consent was obtained from all patients prior to study participation. MRI scans were performed on a 3T MRI scanner (Philips Medical System, Cleveland, Ohio) equipped with a 32-channel phased array head coil at the University of Texas Southwestern Advanced Imaging Research Center. In some implementations, participants first underwent a hypercapnia calibration experiment, followed by resting MRI scans wherein they focused their attention on a central fixation cross for the scan duration. During the resting scan, a dual-echo calibrated functional MRI (cfMRI) pulse sequence was implemented. Following the rest scan, high resolution 3D $T_2$-weighted fluid attenuated inversion recovery (3D $T_2$ FLAIR), $T_1$_weighted magnetization-prepared rapid acquisition gradient-echo (MPRAGE), and diffusion kurtosis imaging (DKI) were performed.

In the hypercapnia calibration experiment, participants underwent a 10-minute scan using dual echo fMRI for calibration (to calculate M; see section 4.5). Participants were given a mouth-piece and a nose clip to ensure that they were only able to breathe by mouth. The mouth-piece delivered either room air or carbogen (5% $CO_2$ and 95% room air). The first 4 minutes consisted of room air (normocapnia portion), and the latter 6 minutes consisted of carbogen solution (hypercapnia portion). Normocapnia and hypercapnia portions of the experiment were controlled manually using a valve switch. End-tidal $CO_2$, breathing rate, heart rate, and arterial $O_2$ saturation from participants were monitored during both conditions to ensure patient safety.

In some implementations, anatomical MPRAGE images were acquired for all participants using a 1 mm isotropic resolution sequence (repetition time (TR)=8.1 ms (fast field gradient echo), echo time (TE)=3.7 ms, sagittal slice orientation, 12 flip angle, 256×256×160 mm field of view (FOV)).

In some implementations, high resolution, 3D $T_2$ FLAIR images were acquired to isolate MS lesions in 3D space to study their shape and surface topology (TR=4800 ms TE=344 ms 1.1 $mm^3$ isotropic resolution with no slice gap, 250×250×179.3 mm FOV, sagittal slice orientation).

In some implementations, dual-echo cfMRI included both pseudo-continuous arterial spin labeling (pCASL; Echo 1, to obtain CBF) and BOLD images (Echo 2). This technique permitted the near-simultaneous acquisition of BOLD and CBF data. The parameters used were as follows: Echo 1: labeling duration 1400 ms, labeling RF flip angle 18°, labeling gap=63.5 mm, 3.44×3.44×6 mm voxel size, TR=4, 006 ms, TE=13 ms, 1450 ms post label delay, 0 mm slice gap. Echo 2: 90° flip angle, 3.44×3.44×6 mm voxel size, TR=4,006 ms, TE=30 ms, 0 mm slice gap.

In some implementations, DKI data were used to measure white matter microstructure integrity. Data were acquired using a single-shot echo planar imaging (EPI) sequence with repetition time (TR)=6500 ms, echo time (TE)=62 ms, resolution=2.0×2.0 $mm^2$, field of view (FOV)=224×224 $mm^2$, slice thickness=2.20 mm, number of slices=62 axial, gap=0 mm, SENSE-reduction factor=2.3, and scan time of approximately 15 min. Three b-shells were acquired (b=0 $s/mm^2$, 1000 $s/mm^2$ and 2500 $s/mm^2$) across 30 directions.

3. 3D Lesion Reconstruction Using High Resolution FLAIR

In some implementations, as best shown in FIG. 3A, lesion segmentation was performed using in-house designed software allowing for its direct extraction in 3D space. Focal brain lesions (n=109) were identified from simultaneously viewed 3D high-resolution $T_1$_weighted, $T_2$-weighted, and FLAIR sequences. All segmentations were performed on supratentorial lesions from 3D $T_2$ FLAIR images by implementing geodesic active contour methodology. All selected ROI files were exported into stereolithography format for further analysis.

4. Cerebral Physiology in and Around MS Lesions a. Regions of Interest

Cerebral physiology was studied in the lesion and regions around the lesion. In some implementations, as shown in FIG. 3B, regions around the lesion were defined as 3 mm voxel layers concentrically (e.g., 104, 108). The first concentric layer immediately adjacent to the surface of the lesion constituted perimeter 1 (e.g., 104). The second, third and fourth layer surrounding the surface of the lesion constituted perimeters 2, 3 and 4 respectively. Regions in the perimeters 1-4 that fell within ventricles and cranium were removed.

b. Blood Oxygenation and Cerebral Blood Flow (CBF)

In some implementations, Echo 1 and Echo 2 data were pre-processed using Analysis of Functional Neuroimages software. Data were despiked and registered to the fifth functional volume of each dataset's Echo 2 sequence using a heptic polynomial interpolation method to correct for motion. CBF was estimated from Echo 1 images (control and label) using surround subtraction. Echo 2 data were registered to each participant's anatomical data. The transformation matrix from this registration was then applied to Echo 1 data. Data were then visually inspected and corrected for alignment errors. In some implementations, Echoes 1 and 2 data were then spatially smoothed using a Gaussian kernel (FWHM=8 mm) and high-pass filtered (0.0156 Hz).

In some implementations, Echo 1 data (CBF) were then converted to physiologic units in ml/100 g/min using Buxton's General Kinetic Model for Perfusion Quantification. Control images from Echo 1 were used to calculate the equilibrium magnetization of arterial blood (Mo) using asl_calib program. Cerebrospinal fluid (CSF) in the ventricles was used as a reference tissue to calculate Mo due to minimal partial volume effects. CSF ROI was obtained in native space based on surface based atlas using FreeSurfer following cortical reconstruction. Estimated values of CBF were masked within range [0-200] ml/100 g/min to exclude implausible physiologic values. Baseline CBF and BOLD values were then averaged across time to reduce variability and maximize statistical power. Lesion and Perimeter 1-4 masks were applied to average baseline CBF and BOLD maps to obtain average blood oxygenation and CBF in and around MS lesions.

c. BOLD Slope Calculation

BOLD slope is the rate of change of BOLD signal from each focal MS lesion through its associated Perimeters 1-4. In some implementations, BOLD slope in these lesions were calculated using the formula:

$$\text{BOLD slope} = \frac{\sum_{i=region}^{n}(BOLD_i - \overline{BOLD})(T_i - \overline{T})}{\sum_{i=region}^{n}(BOLD_i - \overline{BOLD})} \qquad \text{Eq. 1}$$

where regions are the lesions and their associated perimeters, n is the number of regions, $BOLD_i$ is the average BOLD signal in the region and $\overline{BOLD}$ is the average BOLD signal across all regions, $T_i$ is the thickness of the concentric layer.

d. Cerebral Metabolic Rate of Oxygen ($CMRO_2$)

Cerebral metabolic rate of oxygen ($CMRO_2$) reflects the rate of cellular oxygen consumption. In some implementations, dual echo fMRI provided near-simultaneous measures of CBF and BOLD. Together, CBF and BOLD along with biophysical modeling procedures allowed for estimation of the $CMRO_2$ using the deoxyhemoglobin dilution model of BOLD signal change (see Equation 2).

$$\frac{\Delta BOLD}{BOLD_0} = M\left(1 - \left[\frac{\Delta CMRO_2}{CMRO_{2|0}}\right]^{\beta}\left[\frac{\Delta CBF}{CBF_0}\right]^{\alpha-\beta}\right) \qquad \text{Eq. 2}$$

where $\alpha=0.38$ is an empirically-derived constant linking CBF and cerebral blood volume, and $\beta=1.3$ is an empirically-derived constant related to vascular exchange and susceptibility of deoxyhemoglobin at 3T. M is a subject-specific scaling factor dependent upon the washout of resting deoxyhemoglobin determined by a calibration experiment.

Hypercapnia alters vasculature independent of neural activity. Hypercapnia induced through CO2 inhalation causes vasodilation resulting in maximum CBF and BOLD signal. In the hypercapnic physiologic state, cellular oxygen utilization approximates to zero (i.e. $\Delta CMRO_2=0$). In some implementations, hypercapnia induced changes in BOLD and CBF, measured using dual-echo fMRI, were used to calculate, subject-dependent scaling factor M using Equation 3.

$$M = \frac{\frac{\Delta BOLD}{BOLD_0}}{\left(\frac{CBF}{CBF_0}\right)^{\alpha-\beta}} \qquad \text{Eq. 3}$$

e. Calculating M and $CMRO_2$

In some implementations, data from the hypercapnia scan (Echo 1 and Echo 2) were processed in a method similar to that described in section 4.b. Hypercapnia induced changes in BOLD signal ($\Delta BOLD$) and CBF ($\Delta CBF$) from normocapnic baseline were calculated. In order to yield a local estimate of maximum $\Delta BOLD$ and $\Delta CBF$ signal, overlapping top 30% of the $\Delta BOLD$ and top 30% of the $\Delta CBF$ were utilized to calculate M from equation 3. Using M, $CMRO_2$ in and around MS lesions were calculated using the average BOLD and CBF data obtained from resting dual-echo fMRI (see Equation 4).

$$\frac{CMRO_2}{CMRO_{2|gm}} = \left(1 - \frac{\frac{\Delta BOLD}{BOLD_{gm}}}{M}\right)^{\frac{1}{\beta}}\left(\frac{CBF}{CBF_{gm}}\right)^{1-\frac{\alpha}{\beta}} \qquad \text{Eq. 4}$$

5. Diffusion Metrics

In some implementations, DKI images were corrected for eddy-current distortions and motion using FMRIB Software Library (FSL v5.0.9; Oxford, UK) EDDY tool and co-registered via Analysis of Functional Neuroimages package (AFNI) to each participants' MPRAGE anatomical image. Diffusion and kurtosis tensors were estimated using the Diffusion Kurtosis Estimator (DKE) software and DTI and DKI indices were calculated: mean diffusivity (MD), axial diffusivity (AD), radial diffusivity (RD), fractional anisotropy (FA), mean kurtosis (MK), axial kurtosis (AK), and radial kurtosis (RK).

6. Analysis of Lesion Shape and Surface Characteristics

In some implementations, lesion size, shape, and texture were measured using 3D lesion stereolithography files. In some implementations, lesion texture was estimated by analyzing the probability density function corresponding to the cube root of a tetrahedron area obtained by randomly sampling $1 \times 10^6$ tetrahedrons from the surface of studied lesions. The probability density function was separated into 300 equally spaced bins.

7. Manifold Harmonics Transform

Figure 7:
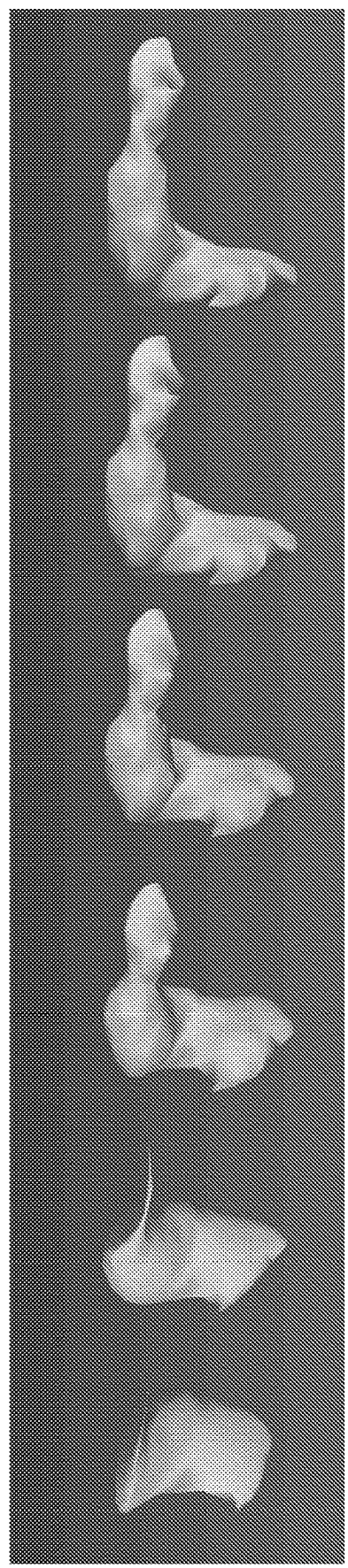
FIG. 7 shows an example of a reconstructed lesion model by using different numbers of eigenvectors: 6, 10, 50, 100, 300, and the original shape, respectively.

In some implementations, manifold harmonics transform (MHT) descriptors were used to quantify lesion shape. The MHT utilizes the eigenvectors of the Laplace-Beltrami operators to convert a 3D lesion geometry into frequency space. Such conversion permitted quantification of lesion shape differences. For numerical computation of eigenvalues and eigenvectors, a finite element modeling method was used to compute a discrete Laplacian for each manifold mesh of a lesion. Finally, the eigenvalues were sorted in ascending order and the first 300 eigenvectors were picked corresponding to the smallest eigenvalues to reconstruct the original shape of lesion. As shown in FIG. 7, a reconstructed lesion model is created by using different numbers of eigenvectors: 6, 10, 50, 100, 300, and original shape, respectively.

a. S.1 Laplace-Beltrami Operator

For a closed surface S, let $\Delta$ denote its Laplace-Beltrami differential operator. The manifold harmonics spectrum is defined as a family of eigenvalues of the Helmholtz equation:

$$\Delta f = -\Delta f \qquad \text{Eq. S1}$$

The "−" sign is required for eigenvalues to be positive. We assume that eigenvalues are distinct and in ascending order:

$$\Delta_0 = 0 < \lambda_1 < \lambda_2 < \ldots \qquad \text{Eq. S2}$$

The eigenvectors $[\varphi_0, \varphi_1, \varphi_2 \ldots]$ corresponding to its different eigenvalues are orthogonal and can be used to reconstruct any given function:

$$f = c_0 \varphi_0 + c_1 \varphi_1 + c_2 \varphi_2 + \ldots \qquad \text{Eq. S3}$$

Thus, eigenvectors of continuous Laplace-Beltrami operator give an orthogonal basis for the space of function defined on the surface.

b. S.2 Discrete Calculation

In order to get Laplacian eigenvalues from discrete mesh, finite element method was used. Based on the definition of the discrete Laplace-Beltrami differential operator, given a function $f$ defined on the surface, the value of $\Delta f$ is approximated as:

$$\Delta f(p_i) \approx \frac{1}{S_i} \sum_{j \in N(i)} \frac{\cot \alpha_{i,j} + \cot \beta_{i,j}}{2} [f(p_j) - f(p_i)] \qquad \text{Eq. S4}$$

Figure 8:
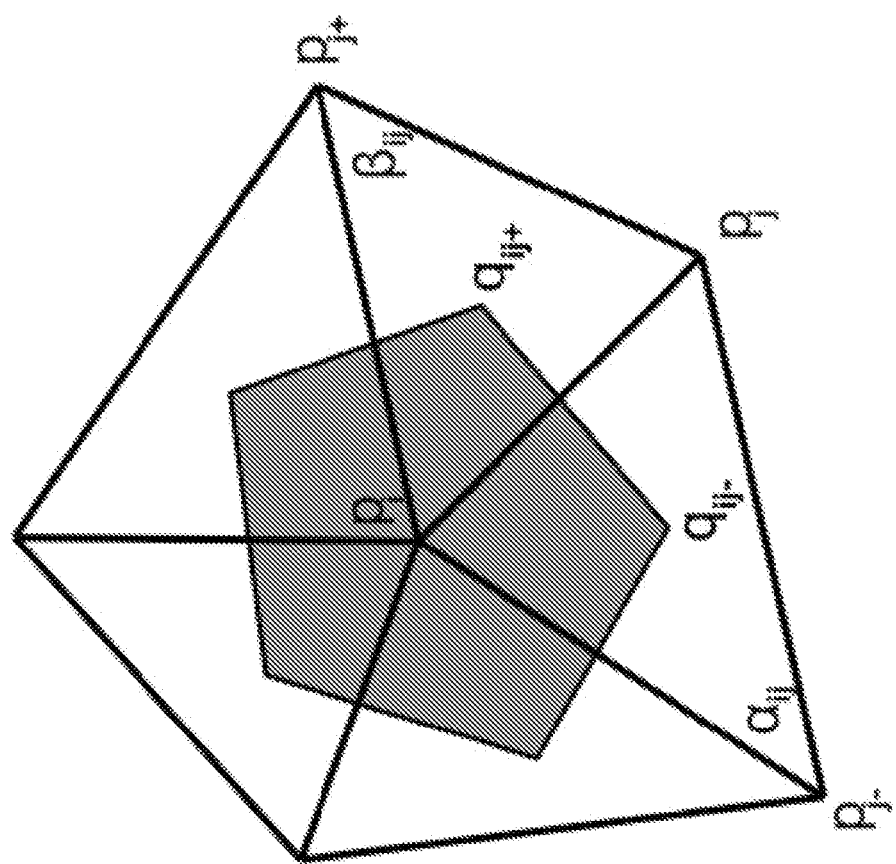
FIG. 8 shows the definition of the angles and area covered by each vertex in order to compute Laplacian eigenvalues for each manifold mesh of a lesion.

As shown if FIG. 8, the angles and area covered by each vertex in order to compute Laplacian eigenvalues for each manifold mesh of a lesion are defined. $S_i$ is the covered region by each vertex. By incorporating Eq. S4 and using the discrete column vector form, the eigenvalue problem of Eq. S1 can be written as:

$$S^{-1}MH = \lambda H \qquad \text{Eq. S5}$$

where M is called the stiffness matrix defined by:

$$\begin{cases} M_{i,j} = \frac{\left(\cot(\beta_{i,j}) + \cos(\dot{\beta}_{i,j})\right)}{2} \\ M_{i,i} = \sum_j M_{i,j} \end{cases} \qquad \text{Eq. S6}$$

and diagonal lumped mass matrix S is defined by the neighboring triangles t of each vertex and their area |t|:

$$S_{i,i} = \sum_{t \in St(i)} \frac{|t|}{3} \qquad \text{Eq. S7}$$

After eigenvalue decomposition using ARPACK, for each manifold mesh surface, we get a set of eigenvalues $\lambda$ and their corresponding vectors H.

c. S.3 Manifold Harmonics Transform (MHT) Descriptor

The geometrical coordinates of a manifold mesh x, y or z was taken as a linear combination of the "hat" basis functions $\phi^i$ defined on the triangulated surface with n vertices of a 3D lesion.

$$x = \sum_{i=1}^{n} x_i \phi^i \qquad \text{Eq. 5}$$

where $x_i$ is the geometric coordinate x at vertex i.

The MHT converts the lesion geometry x, y or z in the "hat" basis function ($\phi^i$) into different frequencies of manifold harmonics ($H^k$). The MHT of x is given by:

$$\tilde{x}_k = \langle x, H^k \rangle = x^T S H^k = \sum_{i=1}^{n} x_i S_{i,i} H_i^k \qquad \text{Eq. 6}$$

where x is the vector of $[x_1, x_2, \ldots, x_n]$ and S is the lumped mass matrix (see supplemental). The inverse MHT transforms the frequencies $[\tilde{x}_1, \tilde{x}_2, \ldots, \tilde{x}_m]$ back to geometric space coordinates $[x_1, x_2, \ldots, x_n]$. The reconstructed coordinate x at vertex i is given by:

$$x_i = \sum_{k=1}^{m} \tilde{x}_k H_i^k \qquad \text{Eq. 7}$$

To make the descriptor invariant to rotation of the 3D lesion, the coefficient magnitude was taken as embedding function $$\tilde{c}_i = \sqrt{\tilde{x}_i^2 + \tilde{y}_i^2 + \tilde{z}_i^2} \qquad \text{Eq. 8}$$

The embedded MHT vector $\tilde{c} = [\tilde{c}_1, \tilde{c}_2, \ldots, \tilde{c}_m]$ was taken as the descriptor to express the shape for each lesion.

8. Conventional Lesion Measures (Lesion Burden, Lesion Location and Lesion Type)

In some implementations, lesion burden was calculated using the lesion prediction algorithm (Schmidt, 2017, Chapter 6.1) as implemented in the LST toolbox version 2.0.15 (www.statistical-modelling.de/lst.html) for SPM. In some implementations, anatomical lesion location and lesion type were manually defined by an MS specialist (e.g., D.O.).

9. Statistical Analyses

All analyses were performed in R (version 3.4.3) and SPSS (version 24.0). Two-way mixed ANOVA models were performed to test the effects of between- or within-subject factors on physiologic variables, BOLD, CBF or $CMRO_2$. The between-subjects factors were type (simulated/focal lesions or MA/MI), and the within-subjects factors were regions namely lesion and Perimeters 1-4. For all models, there were no outliers, as assessed by boxplot. The data were normally distributed, as assessed by Shapiro-Wilk's test of normality. There were homogeneities of variance, as assessed by Levene's test. Mauchly's test of sphericity indicated that the assumption of sphericity was violated for the two-way interaction. Post-hoc tests were performed using one-way ANOVA and they were corrected for multiple comparison using Bonferroni. Metabolically active and inactive lesion type differences for kurtosis tensors were tested using one-way ANOVA.

Since the probability distribution of the cube root of the area of the tetrahedron obtained from sampling a million data points from the lesion surface is non-linear, the data was log quantile density (LQD) transformed. Due to Gaussian assumption violation of functional ANOVA, $L^2$-norm-based bootstrap tests based on 10,000 bootstrap samples to test for mean LQD differences between the two groups was chosen. The $L^2$-norm-based bootstrap test was performed via the fdANOVA package in R. Group differences in the MHT descriptors was tested using multivariate nonparametric analyses due to evidence against the multivariate normality assumption of MANOVA. Multivariate nonparametric analyses were performed using the npmv package in R.

C. MS and NSWM Disease States

As is known in the art, the diagnostic criteria for MS requires the presence of white matter lesions seen on MRI with appropriate size, morphology, and spatial or temporal dissemination pattern. As is also known, such criteria, however, are limited by false positive diagnosis due to the presence of similar MRI findings in NSWM disease states such as migraines and small vessel diseases. The co-existence of age-related vascular changes (i.e., NSWM changes) has been recognized in MS patients, and these comorbidities pose a further diagnostic challenge.

A study was conducted to assess whether accessing BOLD signal and CBF within and around lesions in 3D would inform on the origin and distinguish MS and NSWM lesions irrespective of disease states. The study cohort is described in Table 3.

TABLE 3

| Characteristics | MS patients (N = 23) | NSWM patients (N = 13) |
|---|---|---|
| Age (years) Median (range) | 50.1 (29.6-61.4) | 53.9 (37.8-64.4) |
| Female sex No. (%) | 17 (74%) | 13 (100%) |
| Disease duration (years) Median (range) | 11.3 (1.2-30.8) | |
| Patients on disease modifying therapy No. (%) | 16 (69.6%) | |
| Age at diagnosis (years) Median (range) | 38 (26-54) | |
| Time since last acute exacerbation (years) Median (range) | 2.8 (0.4-13.3) | |
| EDSS score Median (range) | 2.5 (1-7.5) | |
| Total lesion volume (ml) Median (range) | 3.035 (0.12-26.32) | 1.3428 (0.27-13.0863) |

105 NSWM lesions from 13 NSWM disease (NSWMD) patients and 143 MS lesions from 23 relapsing-remitting MS patients were studied. The inclusion criteria for NSWMD patients were as follows: (i) male or female patients between the ages of 18 and 65, (ii) a history of migraine headaches or small vessel disease risk factors, (iii) focal bilateral supratentorial white matter abnormalities on MRI that are atypical for in-situ demyelination (confirmed by a board-certified neuroradiologist) and, (iv) the exclusion of a diagnosis of MS by a specialist (D.T.O) based on clinical impressions, radiological features, and the results from other paraclinical studies.

In this study, the average BOLD signal in the lesion, perimeter-1, and perimeter-2 were obtained as the contrast-to-noise ratio of Echo 2 data. The contrast-to-noise ratio was calculated as the difference between the mean Echo-2 signal in the ROI and the mean Echo-2 signal in the extracranium (noise) divided by the standard deviation of the Echo-2 signal in the extracranium.

Figure 9B:
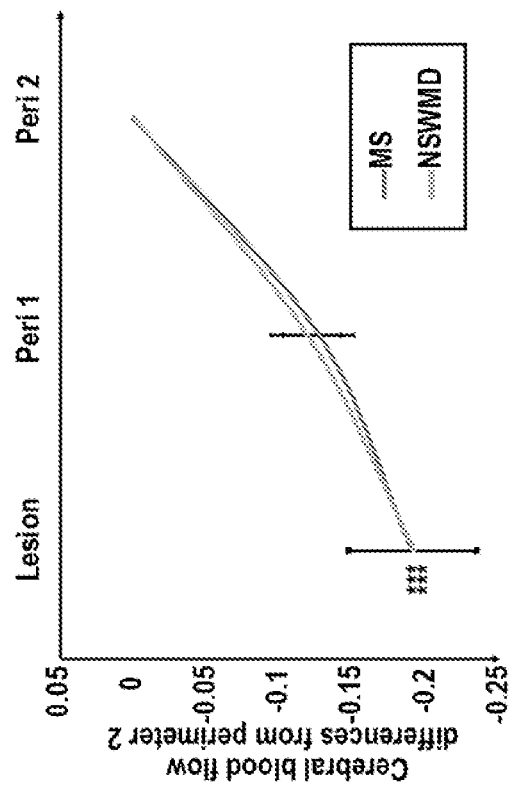
FIG. 9B depicts a graph of mean cerebral blood flow (CBF) in MS lesions and their perimeters and NSWM lesions and their perimeters.
Figure 9A:
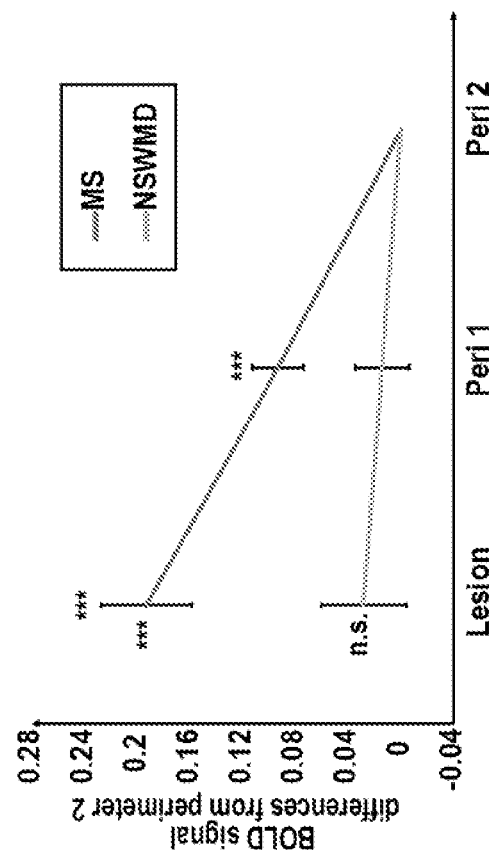
FIG. 9A depicts a graph of mean BOLD signals in MS lesions and their perimeters and in non-specific white matter (NSWM) lesions and their perimeters.

1. BOLD Signal within and Around was Altered in MS Lesions Compared to NSWMD Lesions In some implementations, an assessment was made of the changes in blood oxygenation within and around lesions by testing for changes in the BOLD signal sequentially moving from lesions to their perimeters between MS and NSWMD lesions. The hypothesis of group-differences in BOLD signal changes from lesions to their perimeters was tested using a 3 (Region) by 2 (Group) mixed ANOVA. For MS patients, a significant reduction in the BOLD signal from the lesion to their perimeters was observed, $F(1.104, 156.775)=29.290$, $p<0.0005$, partial $\eta 2=0.171$, as shown in FIG. 9A. FIG. 9A illustrates mean BOLD signal in lesions and their perimeters for MS and NSWM lesions. No such changes in the BOLD signal were observed in NSWMD lesions, $F(1.084, 112.698)=0.7321$, $p=0.4043$, partial $\eta 2=0.0069$. There was a significant Group by Region interaction in BOLD signal, $F(1.101, 270.748)=10.614$, $p=0.0008$, partial $\eta 2=0.041$. NSWMD lesions had significantly higher BOLD signals within lesion tissue (MMS=11.55, SDMS=1.74, MNSWM=12.40, SDNSWM=1.51), $F(1, 246)=16.045$, $p=0.0001$, partial $\eta 2=0.061$, and at perimeter 1 (MMS=11.45, SDMS=1.67, MNSWM=12.38, SDNSWM=1.49), $F(1, 246)=20.274$, $p<0.0005$, partial $\eta 2=0.078$, when compared to MS lesions.

2. BOLD Slope was Significantly Lower in NSWMD Lesions Compared to MS Lesions

Figure 9D:
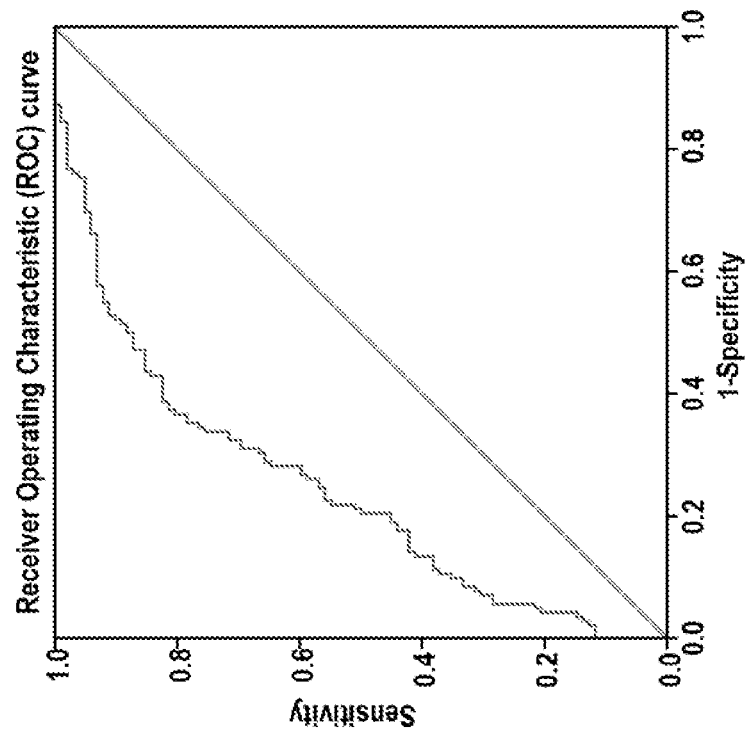
FIG. 9D depicts a receiver operator characteristic (ROC) curve for a model.
Figure 9C:
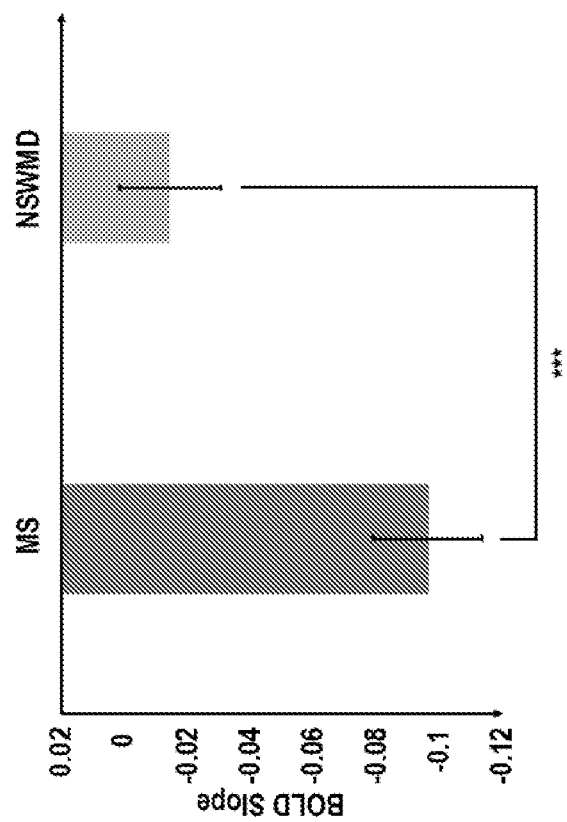
FIG. 9C depicts a bar graph of mean BOLD slope for MS lesions and NSWM lesions.

As explained above, BOLD slope can be an indicator of metabolic capacity within and around MS lesions. In some implementations, metabolic differences between MS and NSWM lesions were assessed by testing for group-differences in BOLD slope using an independent-sample t-test. BOLD slope was significantly lower in MS lesions (MMS=−0.0963, SDMS=0.2073) compared to NSWMD lesions (MNNSWMD=−0.0142, SDNSWMD=0.1656, $t(246)=−3.347$, $p=0.0009$), as shown in FIG. 9C. FIG. 9C illustrates a bar graph representing mean BOLD slope for MS and NSWM lesions.

3. CBF was not Altered within and Around MS and NSWMD Lesions

In some implementations, an assessment was made of the changes in CBF within and around lesions by testing for changes in CBF sequentially moving from lesions to their perimeters between MS and NSWMD lesions. The hypothesis of group-differences in CBF changes from lesions to their perimeters was tested using a 3 (Region) by 2 (Group) mixed ANOVA. In some implementations, CBF sequentially reduced from perimeters to lesions in MS and NSWM, as shown in FIG. 9B. FIG. 9B illustrates the mean CBF in lesions and their perimeters for MS and NSWM lesions. CBF significantly reduced moving from perimeters to their lesions for both MS, $F(1.117, 158.595)=15.487$, $p<0.0005$, partial $\eta 2=0.098$ and NSWM lesions, $F(1.050, 109.233)=5.182$, $p=0.0063$, partial $\eta 2=0.047$. There was no significant Group x Region interaction in CBF, $F(1.085, 266.994)=0.428$, $p=0.5299$, partial $\eta 2=0.002$. There were no group-differences in CBF in the lesion tissue, and perimeter 1 (all $p>0.05$).

4. BOLD Signal within and Around Lesions Significantly Distinguished NSWM from MS Lesions In some implementations, an assessment was made of whether blood oxygenation within and around MS lesions could inform on the origin of the observed white matter lesions (i.e., MS, NSWMD). To test this hypothesis, binomial logistic regression was performed with Groups as a dependent variable and BOLD Signal in the Lesion, Perimeter 1, Perimeter 2, BOLD Signal Differences between Perimeter 1 and Lesion, and BOLD Signal Differences between Perimeter 2 and Perimeter 1 were independent variables. In some implementations, the logistic regression model was statistically significant, $\chi 2(3)=54.670$, $p<0.0005$. The model explained 27.0% (Nagelkerke $R2$) of the variance in disease states. The specificity of the model in identifying NSWM lesion was 78.9%. The sensitivity was 50.0%, the positive predictive value (i.e., the probability that a lesion classified as NSWM truly is NSWM) was 62.9%, and the negative predictive value (i.e., the probability that a lesion classified as not NSWM is truly not NSWM) was 68.7%. Of the five predictor variables only two were statistically significant: BOLD signal in lesion (B=0.597, SE=0.108, $p<0.0005$) and BOLD signal difference between perimeter 1 and lesion (B=0.4152, SE=1.365, $p=0.0023$). FIG. 9D shows the receiver operator characteristic (ROC) curve for the model. The area under the ROC curve was 0.761 (95% CI, 0.701 to 0.820).

Figure 10B:
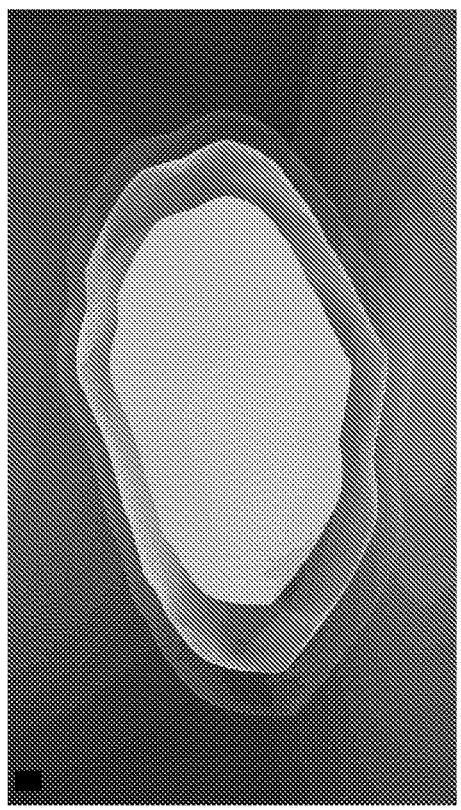
FIG. 10B shows a three-dimensional illustration of an NSWM lesion and its perimeters.
Figure 10A:
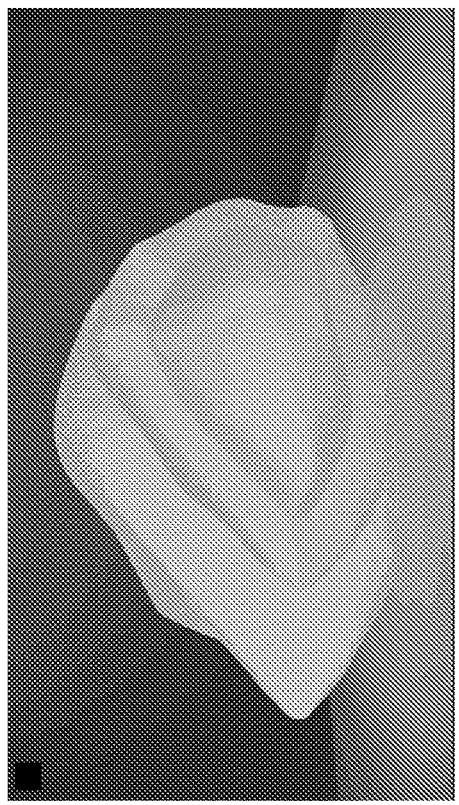
FIG. 10A shows a three-dimensional illustration of an MS lesion and its perimeters.

FIG. 10A illustrates a 3D illustration of a MS lesion and its perimeters. FIG. 10B illustrates a 3D illustration of a NSWM lesion and its perimeters. The grey gradient represents change in BOLD signal from perimeter-2 towards the lesion.

Thus, the study undertook a novel 3D approach to investigate the integrity of surrounding brain tissue by assessing the physiology within lesions and their surroundings exact to the 3D shape of lesions. This approach was applied to distinguish two disease states that might, at times, yield similar-appearing radiological data. The utility of BOLD signal within and around MS lesions to distinguish the two disease states at the level of individual lesion was identified. Thus, this technique shows promise for clinical utility to distinguish the two disease states and effectively adds to other methods that aim to improve the specificity in identifying the etiology of central nervous system lesions to optimize the quality of medical management provided to patients.

The above specification and examples provide a complete description of the structure and use of exemplary configurations. Although certain configurations have been described above with a certain degree of particularity, or with reference to one or more individual configurations, those skilled in the art could make numerous alterations to the disclosed configurations without departing from the scope of this invention. As such, the various illustrative configurations of the present devices, apparatuses, kits, and methods are not intended to be limited to the particular forms disclosed. Rather, they include all modifications and alternatives falling within the scope of the claims, and configurations other than the one shown may include some or all of the features of the depicted configuration. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one configuration or may relate to several configurations.

The claims are not intended to include, and should not be interpreted to include, means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth herein, are specifically incorporated herein by reference.

[1] T. Vos, "Articles Global, regional, and national burden of neurological disorders during 1990-2015: a systematic analysis for the Global Burden of Disease Study 2015," *Lancet Neurol*, vol. 16, pp. 877-97, 2017.

[2] L. K. Fisniku et al., "Disability and $T_2$ MRI lesions: a 20-year follow-up of patients with relapse onset of multiple sclerosis," *Brain*, vol. 131, no. 3, pp. 808-817, February 2008.

[3] A. Rovira and A. León, "MR in the diagnosis and monitoring of multiple sclerosis: An overview," *Eur J Radiol*, vol. 67, no. 3, pp. 409-14, 2008.

[4] Y. Ge, "Multiple sclerosis: the role of MR imaging," *AJNR Am J Neuroradiol*, vol. 27, no. 6, pp. 1165-1176, 2006.

[5] S. Datta, B. R. Sajja, R. He, R. K. Gupta, J. S. Wolinsky, and P. A. Narayana, "Segmentation of gadolinium-enhanced lesions on MRI in multiple sclerosis," *J. Magn. Reson. Imaging*, vol. 25, no. 5, pp. 932-937, 2007.

[6] F. Fazekas, F. Barkhof, and M. Filippi, "Unenhanced and enhanced magnetic resonance imaging in the diagnosis of multiple sclerosis.," *J. Neurol. Neurosurg. Psychiatry*, vol. 64, no. Suppl 1, pp. S2-5, 1998.

[7] R. Geraldes et al., "The current role of MRI in differentiating multiple sclerosis from its imaging mimics," *Nat. Rev. Neurol.*, vol. 14, no. 4, pp. 199-213, March 2018.

[8] A. J. Solomon et al., "The contemporary spectrum of multiple sclerosis misdiagnosis: A multicenter study.," *Neurology*, vol. 87, no. 13, pp. 1393-9, September 2016.

[9] D. Goldberg-Zimring, H. Azhari, S. Miron, and A. Achiron, "3-D surface reconstruction of multiple sclerosis lesions using spherical harmonics," *Magn. Reson. Med.*, vol. 46, no. 4, pp. 756-766, October 2001.

[10] B. D. Newton et al., "Three-Dimensional Shape and Surface Features Distinguish Multiple Sclerosis Lesions from Nonspecific White Matter Disease," *J. Neuroimaging*, vol. 27, no. 6, pp. 613-619, 2017.

[11] D. Goldberg-Zimring, A. Achiron, C. R. G. Guttmann, and H. Azhari, "Three-Dimensional Analysis of the Geometry of Individual Multiple Sclerosis Lesions: Detection of Shape Changes Over Time Using Spherical Harmonics."

[12] M. R. Hansen et al., "Post-gadolinium 3-dimensional spatial, surface, and structural characteristics of glioblastomas differentiate pseudoprogression from true tumor progression," *J. Neurooncol.*, pp. 1-8, June 2018.

[13] L. J. Bagley, R. I. Grossman, S. L. Galetta, G. P. Sinson, M. Kotapka, and J. C. McGowan, "Characterization of white matter lesions in multiple sclerosis and traumatic brain injury as revealed by magnetization transfer contour plots," *Am. J. Neuroradiol.*, vol. 20, no. 6, pp. 977-981, 1999.

[14] J. T. Chen et al., "Local magnetization transfer ratio signal inhomogeneity is related to subsequent change in MTR in lesions and normal-appearing white-matter of multiple sclerosis patients," *Neuroimage*, vol. 25, no. 4, pp. 1272-1278, 2005.

[15] S. D. Wolff and R. S. Balaban, "Magnetization transfer contrast (MTC) and tissue water proton relaxation in vivo," *Magn. Reson. Med.*, vol. 10, no. 1, pp. 135-144, April 1989.

[16] N. M. Moll et al., "Multiple sclerosis normal-appearing white matter: Pathology-imaging correlations," *Ann. Neurol.*, vol. 70, no. 5, pp. 764-773, 2011.

[17] J. Lee, R. Fox, A. Chang, and R. M. Ransohoff, "Multiple Sclerosis Normal-Appearing White Matter: Pathology-Imaging Correlations," *Ann Neurol*, vol. 70, no. 5, pp. 764-773, 2012.

[18] C. F. Lucchinetti, W. Brück, J. E. Parisi, B. W. Scheithauer, M. Rodriguez, and H. Lassmann, "Heterogeneity of Multiple Sclerosis Lesions: Implications for the Pathogenesis of Demyelination," *Ann. Neurol.*, vol. 47, no. 6, pp. 707-717, 2000.

[19] C. Lucchinetti et al., "Heterogeneity of Multiple Sclerosis Lesions: Implications for the Pathogenesis of Demyelination."

[20] P. Patrikios et al., "Remyelination is extensive in a subset of multiple sclerosis patients," Brain, vol. 129, no. 12, pp. 3165-3172, June 2006.

[21] B. D. Trapp, J. Peterson, R. M. Ransohoff, R. Rudick, S. Mörk, and L. Bo, "Axonal Transection in the Lesions of Multiple Sclerosis," N. Engl. J. Med., vol. 338, no. 5, pp. 278-285, January 1998.

[22] R. D. Hoge, J. Atkinson, B. Gill, G. R. Crelier, S. Marrett, and G. B. Pike, "Investigation of BOLD Signal Dependence on Cerebral Blood Flow and Oxygen Consumption: The Deoxyhemoglobin Dilution Model."

[23] R. B. Buxton, K. Uludag, D. J. Dubowitz, and T. T. Liu, "Modeling the hemodynamic response to brain activation," 2004.

[24] C. J. Gauthier and R. D. Hoge, "Magnetic resonance imaging of resting OEF and $CMRO_2$ using a generalized calibration model for hypercapnia and hyperoxia," Neuroimage, vol. 60, no. 2, pp. 1212-1225, 2012.

[25] C. J. Gauthier and R. D. Hoge, "A generalized procedure for calibrated MRI incorporating hyperoxia and hypercapnia," Hum. Brain Mapp., vol. 34, no. 5, pp. 1053-1069, 2013.

[26] N. De Stefano, P. M. Matthews, J. P. Antel, M. Preul, G. Francis, and D. L. Arnold, "Chemical pathology of acute demyelinating lesions and its correlation with disability," Ann. Neurol., vol. 38, no. 6, pp. 901-909, December 1995.

[27] M. Filippi et al., "Association between pathological and MRI findings in multiple sclerosis," 2012.

[28] F. Barkhof et al., "Remyelinated Lesions in Multiple Sclerosis," Arch. Neurol., vol. 60, no. 8, p. 1073, August 2003.

[29] J. W. Prineas, R. O. Barnard, T. Revesz, E. E. Kwon, L. Sharer, and E.-S. Cho, "Multiple sclerosis," Brain, vol. 116, no. 3, pp. 681-693, June 1993.

[30] D. McAlpine and A. Compston, "McAlpine's Multiple Sclerosis," in McAlpine's Multiple Sclerosis, 2005, pp. 83-91.

[31] D. Goldberg-Zimring, B. Shalmon, K. H. Zou, H. Azhari, D. Nass, and A. Achiron, "Assessment of Multiple Sclerosis Lesions with Spherical Harmonics: Comparison of MR Imaging and Pathologic Findings 1."

[32] C. Lucchinetti, W. Brück, J. Parisi, B. Scheithauer, M. Rodriguez, and H. Lassmann, "A quantitative analysis of oligodendrocytes in multiple sclerosis lesions. A study of 113 cases," Brain, vol. 122, no. 12, pp. 2279-2295, 1999.

[33] B. D. Trapp and P. K. Stys, "Virtual hypoxia and chronic necrosis of demyelinated axons in multiple sclerosis," www.thelancet.com/neurology, vol. 8, 2009.

[34] R. Dutta et al., "Mitochondrial Dysfunction as a Cause of Axonal Degeneration in Multiple Sclerosis Patients," Ann Neurol, vol. 59, pp. 478-489, 2006.

[35] P. Belov et al., "Lower Arterial Cross-Sectional Area of Carotid and Vertebral Arteries and Higher Frequency of Secondary Neck Vessels Are Associated with Multiple Sclerosis.," AJNR. Am. J. Neuroradiol., vol. 39, no. 1, pp. 123-130, January 2018.

[36] A. Chang, A. Nishiyama, J. Peterson, J. Prineas, and B. D. Trapp, "NG2-positive oligodendrocyte progenitor cells in adult human brain and multiple sclerosis lesions.," J. Neurosci., vol. 20, no. 17, pp. 6404-6412, 2000.

[37] M. L. Cuzner and W. T. Norton, "Biochemistry of demyelination," in Brain Pathology, 1996, vol. 6, no. 3, pp. 231-242.

[38] J. J. Harris and D. Attwell, "Cellular/Molecular The Energetics of CNS White Matter."

[39] L. I. Sánchez-Abarca, A. Tabernero, and J. M. Medina, "Oligodendrocytes use lactate as a source of energy and as a precursor of lipids," Glia, vol. 36, no. 3, pp. 321-329, December 2001.

[40] S. Y. Lunt and M. G. Vander Heiden, "Aerobic Glycolysis: Meeting the Metabolic Requirements of Cell Proliferation," Annu. Rev. Cell Dev. Biol., vol. 27, no. 1, pp. 441-464, 2011.

[41] S. Mi, R. Blake Pepinsky, and D. Cadavid, "Blocking LINGO-1 as a Therapy to Promote CNS Repair: From Concept to the Clinic," CNS Drugs, vol. 27, no. 7, pp. 493-503, July 2013.

[42] S. Mi et al., "LINGO-1 antagonist promotes spinal cord remyelination and axonal integrity in MOG-induced experimental autoimmune encephalomyelitis," Nat. Med., vol. 13, no. 10, pp. 1228-1233, October 2007.

[43] F. Sedel et al., "High doses of biotin in chronic progressive multiple sclerosis: A pilot study," Mult. Scler. Relat. Disord., vol. 4, no. 2, pp. 159-169, March 2015.

[44] D. K. Jones, M. A. Horsfield, and A. Simmons, "Optimal strategies for measuring diffusion in anisotropic systems by magnetic resonance imaging," Magn. Reson. Med., vol. 42, no. 3, pp. 515-525, 1999.

[45] R. W. Cox, "AFNI: software for analysis and visualization of functional magnetic resonance neuroimages," Comput. Biomed. Res., vol. 29, no. 29, pp. 162-173, 1996.

[46] T. T. Liu and E. C. Wong, "A signal processing model for arterial spin labeling functional MRI," Neuroimage, vol. 24, no. 1, pp. 207-215, January 2005.

[47] D. C. Alsop et al., "Recommended implementation of arterial spin-labeled perfusion MRI for clinical applications: A consensus of the ISMRM perfusion study group and the European consortium for ASL in dementia," Magn. Reson. Med., vol. 73, no. 1, pp. 102-116, January 2015.

[48] R. B. Buxton, E. C. Wong, and L. R. Frank, "Dynamics of blood flow and oxygenation changes during brain activation: The balloon model," Magn. Reson. Med., vol. 39, no. 6, pp. 855-864, June 1998.

[49] R. S. Desikan et al., "An automated labeling system for subdividing the human cerebral cortex on MRI scans into gyral based regions of interest," Neuroimage, vol. 31, no. 3, pp. 968-980, July 2006.

[50] A. Merola et al., "Mapping the pharmacological modulation of brain oxygen metabolism: The effects of caffeine on absolute $CMRO_2$ measured using dual calibrated fMRI," Neuroimage, vol. 155, pp. 331-343, July 2017.

[51] B. Ances, F. Vaida, R. Ellis, and R. Buxton, "Test-retest stability of calibrated BOLD-fMRI in HIV− and HIV+ subjects," Neuroimage, vol. 54, no. 3, pp. 2156-2162, February 2011.

[52] O. Leontiev and R. B. Buxton, "Reproducibility of BOLD, perfusion, and $CMRO_2$ measurements with calibrated-BOLD fMRI," Neuroimage, vol. 35, no. 1, pp. 175-184, March 2007.

[53] J. L. Hutchison, H. Lu, and B. Rypma, "Neural Mechanisms of Age-Related Slowing: The CBF/CMRO2 Ratio Mediates Age-Differences in BOLD Signal and Human Performance," Cereb. Cortex, vol. 23, no. 10, pp. 2337-2346, October 2013.

[54] J. L. R. Andersson, M. S. Graham, E. Zsoldos, and S. N. Sotiropoulos, "Incorporating outlier detection and replacement into a non-parametric framework for movement and distortion correction of diffusion MR images," Neuroimage, vol. 141, pp. 556-572, November 2016.

[55] J. L. R. Andersson and S. N. Sotiropoulos, "An integrated approach to correction for off-resonance effects and subject movement in diffusion MR imaging," *Neuroimage*, vol. 125, pp. 1063-1078, January 2016.

[56] A. Tabesh, J. H. Jensen, B. A. Ardekani, and J. A. Helpern, "Estimation of tensors and tensor-derived measures in diffusional kurtosis imaging," *Magn. Reson. Med.*, vol. 65, no. 3, pp. 823-836, 2011.

[57] B. Vallet and B. Lévy, "Spectral Geometry Processing with Manifold Harmonics," *Comput. Graph. Forum*, vol. 27, no. 2, pp. 251-260, April 2008.

[58] A. Bunn and M. Korpela, "Crossdating in dp1R," 2013.

[59] A. Petersen and H.-G. Müller, "Functional data analysis for density functions by transformation to a Hilbert space," *Ann. Stat.*, vol. 44, no. 1, pp. 183-218, February 2016.

[60] J.-T. Zhang, *Analysis of Variance for Functional Data*. Chapman and Hall/CRC, 2013.

[61] U. Munzel and E. Brunner, "Nonparametric Tests in the Unbalanced Multivariate One-Way Design," *Biometrical J.*, vol. 42, no. 7, pp. 837-854, November 2000.

[62] A. R. Ellis, W. W. Burchett, S. W. Harrar, and A. C. Bathke, "Nonparametric Inference for Multivariate Data: The R Package npmv," *JSS J. Stat. Softw.*, vol. 76, 2017.

[63] A. J. Thompson, B. L Banwell, F. Barkhof, et al., "Diagnosis of multiple sclerosis: 2017 revisions of the McDonald criteria," *Lancet. Neurol.* 17:162-173, 2018.

[64] S. Liu, J. Kullnat, D. Bourdette et al., "Prevalence of brain magnetic resonance imaging meeting Barkhof and McDonald criteria for dissemination in space among headache patients," *Mult. Schler. J.*

[65] U. Seneviratne, W. Chong, P. H. Billimoria, "Brain white matter hyperintensities in migraine: Clinical and radiological correlates," *Clin. Neurol. Neruosurg*, 2013.

[66] M. Absinta, M. A. Rocca, B. Colombo, et al., "Patients with migraine do not have MRI visible cortical lesions," *J. Neurol.*, 2012.

[67] G. Akman-Demir, M. Mutlu, A. Kiyat-Atamer, et al., "Behcet's disease patients with multiple sclerosis-like features: discriminative value of Barkhof criteria," *Clin. Exp. Rheumatol.*, 33:S80-4.

[68] S. S. Kim, D. P. Richman, W. O. Johnson, et al., "Limited utility of current MRI criteria for distinguishing multiple sclerosis from common mimickers: Primary and secondary CNS vasculitis, lupus and Sjogren's syndrome," *Mull. Scler.*, 2014.

[69] R. Schmidt, C. Enziner, S. Ropele, et al., "Subcortical vascular cognitive impairment: Similarities and differences with multiple sclerosis," *J. Neurol. Sci.*, 2006.

[70] R. Geraldes, M. M. Esiri, G. C. Deluca, J. Palace, "Age-related small vessel disease: a potential contributor to neurodegeneration in multiple sclerosis."

[71] M. Welvaert, Y. Rosseel, "On the definition of signal-to-noise ratio and contrast-to-noise ratio for fMRI data," *PLoS One* 8, 2013.

[72] J. S. Hyde, B. B. Biswal, A. Jesmanowicz, "High-resolution fMRI using multislice partial k-space GR-EPI with cubic voxels," *Magn. Reson. Med.*, 46:114-125, 2001.

[73] L. L. Wald, "The future of acquisition speed, coverage, sensitivity, and resolution," *Neuroimage*, 62:1221-1229, 2012.

[74] D. K. Sivakolundu, M. R. Hansen, K. L. West, et al., "Three-Dimensional Lesion Phenotyping and Physiologic Characterization Inform Remyelination Ability in Multiple Sclerosis," *J. Neuroimaging*, 00:1-10, 2019.

The invention claimed is:

1. A system for determining characteristics of a brain lesion and tissue encompassing boundaries surrounding the brain lesion in three dimensions, the system comprising:
   a computer system including at least one processor configured to:
      receive data from a magnetic resonance imaging (MRI) machine configured to generate one or more series of images corresponding to a structural and a functional characteristic of a brain lesion and tissue encompassing one or more enlarged boundaries surrounding the brain lesion, the brain lesion having an outer boundary and at least part of the one or more enlarged boundaries surrounding the brain lesion being offset by a given distance from the outer boundary of the brain lesion;
      segment the received data to isolate a portion of the received data corresponding to the brain lesion and the tissue surrounding the brain lesion within the one or more enlarged boundaries;
      create, based on the segmented data, one or more three-dimensional (3D) models of the brain lesion and the tissue surrounding the brain lesion within the one or more enlarged boundaries;
      analyze, based on the one or more 3D models, one or more 3D phenotypic characteristics of the brain lesion and a slope of a blood oxygen level dependent (BOLD) signal from within the brain lesion through the one or more enlarged boundaries, and
      determine, based on the one or more 3D phenotypic characteristics and the slope, indicators of one or more characteristics selected from a group of characteristics consisting of: lesion age, extent of injury, remyelination capacity, tissue integrity within the brain lesion, tissue integrity within tissue surrounding the brain lesion, and metabolic activity of the brain lesion within tissue surrounding the brain lesion.

2. The system of claim 1, wherein a majority of each of the one or more enlarged boundaries surrounding the brain lesion is offset by a given distance from the outer boundary of the brain lesion.

3. The system of claim 1, wherein all of each of the one or more enlarged boundaries surrounding the brain lesion is offset by a given distance from the outer boundary of the brain lesion.

4. The system of claim 1, wherein the received data includes a series of two-dimensional (2D) images, and the one or more three-dimensional (3D) models is derived from the series of 2D images.

5. The system of claim 4, wherein the at least one processor is configured to give each image in the series of two-dimensional (2D) images a thickness and assemble the 2D images to define the one or more 3D models so as to be capable of being exported into stereolithographic format.

6. The system of claim 1, wherein the at least one processor is configured to determine an indicator of tissue integrity within the brain lesion by measuring white matter microstructure integrity via diffusion kurtosis imaging (DKI).

7. The system of claim 1, wherein the slope of the blood oxygen level dependent (BOLD) signal is calculated using the formula $$\text{BOLD slope} = \frac{\sum_{i=region}^{n}(\text{BOLD}_i - \overline{\text{BOLD}})(T_i - \overline{T})}{\sum_{i=region}^{n}(\text{BOLD}_i - \overline{\text{BOLD}})}$$

wherein regions are the brain lesions and their associated perimeters, n is the number of regions, $BOLD_i$ is the average BOLD signal in the region and $\overline{BOLD}$ is the average BOLD signal across all regions, $T_i$ is the thickness of the concentric voxel layer.

8. The system of claim 1, wherein the at least one processor is also configured to calculate a cerebral metabolic rate of oxygen ($CMRO_2$) using the formula $$\frac{\Delta BOLD}{BOLD_0} = M\left(1 - \left[\frac{\Delta CMRO_2}{CMRO_{2|0}}\right]^\beta \left[\frac{\Delta CBF}{CBF_0}\right]^{\alpha-\beta}\right)$$

wherein $\alpha=0.38$ is an empirically-derived constant linking cerebral blood flow (CBF) and cerebral blood volume; $\beta=1.3$ is an empirically-derived constant related to vascular exchange and susceptibility of deoxyhemoglobin at 3T; and M is a subject-specific scaling factor dependent upon the washout of resting deoxyhemoglobin determined by a hypercapnia calibration experiment.

9. The system of claim 8, wherein the hypercapnia induced changes in the blood oxygen level dependent (BOLD) signal and the cerebral blood flow (CBF) are used to calculate a subject-specific scaling factor M using the formula $$M = \frac{\frac{\Delta BOLD}{BOLD_0}}{\left(\frac{\Delta CBF}{CBF_0}\right)^{\alpha-\beta}}$$

10. The system of claim 9, wherein the subject-specific scaling factor M and the average blood oxygen level dependent (BOLD) and the cerebral blood flow (CBF) data is used to calculate $CMRO_2$ within and around the brain lesion using the formula $$\frac{\Delta CMRO_2}{CMRO_{2|gm}} = \left(1 - \frac{\frac{\Delta BOLD}{BOLD_{gm}}}{M}\right)^{\frac{1}{\beta}} \left(\frac{\Delta CBF}{CBF_{gm}}\right)^{1-\frac{\alpha}{\beta}}$$

11. The system of claim 1, wherein the one or more 3D phenotypic characteristics include lesion volume, lesion surface texture, and/or lesion shape.

12. The system of claim 1, wherein the at least one processor is configured to sort eigenvalues in ascending order and select one or more eigenvectors corresponding to a smallest eigenvalues to reconstruct an original shape of the brain lesion.

13. A method of determining characteristics of a brain lesion and tissue encompassing boundaries surrounding the brain lesion in a patient, the method comprising:
   scanning a portion of the patient with a magnetic resonance imaging (MRI) machine configured to generate data corresponding to a structural and a functional characteristic of a brain lesion of the patient and tissue encompassing one or more enlarged boundaries surrounding the brain lesion, the brain lesion having an outer boundary and at least part of the one or more enlarged boundaries surrounding the brain lesion being offset by a given distance from the outer boundary of the brain lesion;
   segmenting the generated data to isolate the portion of the generated data corresponding to the brain lesion and the tissue surrounding the brain lesion within the one or more enlarged boundaries;
   creating, based on the segmented data, one or more three-dimensional (3D) models of the brain lesion and the tissue surrounding the brain lesion within the one or more enlarged boundaries;
   analyzing, based on the one or more 3D models, one or more 3D phenotypic characteristics of the brain lesion and a slope of a blood oxygen level dependent (BOLD) signal from within the brain lesion through the one or more enlarged boundaries; and
   determining, based on the one or more 3D phenotypic characteristics and the slope, indicators of one or more characteristics selected from a group of characteristics consisting of: lesion age, extent of injury, remyelination capacity, tissue integrity within the brain lesion, tissue integrity within tissue surrounding the brain lesion, and metabolic activity of the brain lesion within tissue surrounding the brain lesion.

14. The method of claim 13, wherein a majority of each of the one or more enlarged boundaries surrounding the brain lesion is offset by a given distance from the outer boundary of the brain lesion.

15. The method of claim 13, wherein all of each of the one or more enlarged boundaries surrounding the brain lesion is offset by a given distance from the outer boundary of the brain lesion.

16. The method of claim 13, wherein the one or more enlarged boundaries surrounding the brain lesion each include a region defined as a 3 mm concentric voxel layer.

17. The method of claim 13, wherein the one or more enlarged boundaries surrounding the brain lesion include a first boundary, a second boundary, a third boundary, and a fourth boundary.

18. The method of claim 13, wherein the scanning further comprises 3D $T_2$-weighted fluid attenuated inversion recovery (3D $T_2$ FLAIR) to isolate the brain lesion to create the one or more three-dimensional (3D) models of the brain lesion and the tissue encompassing the one or more enlarged boundaries surrounding the brain lesion.

19. The method of claim 13, wherein the scanning further comprises $T_1$-weighted magnetization-prepared rapid acquisition gradient-echo (MPRAGE) imaging to produce anatomical images of the brain lesion and the tissue encompassing the one or more enlarged boundaries surrounding the brain lesion.

20. The method of claim 13, wherein the scanning includes diffusion kurtosis imaging (DKI) to measure white matter microstructure integrity within the brain lesion.

21. The method of claim 13, wherein the analyzing includes calculating a cerebral blood flow (CBF) value and a cerebral metabolic rate of oxygen ($CMRO_2$) value.

22. The method of claim 13, wherein the one or more 3D phenotypic characteristics include lesion volume, lesion surface texture, and/or lesion shape.

23. A method of treating brain lesions in a patient, the method comprising:
   administering a treatment to the patient in response to a determination of one or more physiological characteristics of the brain lesions by a method comprising:
      scanning a portion of the patient with a magnetic resonance imaging (MRI) machine configured to generate data corresponding to a structural and a functional characteristic of a brain lesion of the patient and tissue encompassing one or more enlarged boundaries surrounding the brain lesion, the brain lesion having an outer boundary and at least part of the one or more enlarged boundaries surrounding the brain lesion being offset by a given distance from the outer boundary of the brain lesion;

segmenting the generated data to isolate the portion of the generated data corresponding to the brain lesion and the tissue surrounding the brain lesion within the one or more enlarged boundaries;

creating, based on the segmented data, one or more three-dimensional (3D) models of the brain lesion and the tissue surrounding the brain lesion within the one or more enlarged boundaries;

analyzing, based on the one or more 3D models, one or more 3D phenotypic characteristics of the brain lesion and a slope of a blood oxygen level dependent (BOLD) signal from within the brain lesion through the one or more enlarged boundaries; and determining, based on the one or more 3D phenotypic characteristics and the slope, indicators of one or more characteristics selected from a group of characteristics consisting of: lesion age, extent of injury, remyelination capacity, tissue integrity within the brain lesion, tissue integrity within tissue surrounding the brain lesion, and metabolic activity of the brain lesion within tissue surrounding the brain lesion.

24. The method of claim 23, wherein the treatment is switched based on the indicators from a disease modifying therapeutic agent to a different disease modifying therapeutic agent.

25. The method of claim 23, wherein the treatment includes one or more chemotherapeutic drugs and/or immunomodulatory agents.

26. The method of claim 23, further comprising:
determining, based on the one or more 3D phenotypic characteristics and the slope, treatment effects from one or more prescribed therapies and/or one or more investigational medications aimed at myelin, axonal, and/or tissue repair.

27. The method of claim 23, further comprising:
ceasing the treatment if an association of the one or more 3D phenotypic characteristics and the slope suggest disease stability.

28. The method of claim 23, wherein lesion age, extent of injury, remyelination capacity, tissue integrity within the brain lesion, tissue integrity within tissue encompassing one or more enlarged boundaries surrounding the brain lesion, and metabolic activity of the brain lesion and tissue encompassing one or more enlarged boundaries surrounding the brain lesion are determined using artificial intelligence, machine learning, and/or deep learning techniques.

* * * * *